United States Patent [19]

Tezuka et al.

[11] Patent Number: 5,538,688

[45] Date of Patent: *Jul. 23, 1996

[54] CARTRIDGE FOR STORING DRY ANALYTICAL FILM CHIPS

[75] Inventors: Shigeru Tezuka; Yasushi Fujisaki; Hikaru Tsuruta; Osamu Seshimoto; Yoshihiko Abe, all of Saitama, Japan

[73] Assignee: Fuji Photo Film Co., Ltd., Kanagawa, Japan

[*] Notice: The term of this patent shall not extend beyond the expiration date of Pat. No. 5,534,224.

[21] Appl. No.: 51,037

[22] Filed: Apr. 20, 1993

[30] Foreign Application Priority Data

Apr. 20, 1992 [JP] Japan .................. 4-099823

[51] Int. Cl.$^6$ .................. G01N 21/00; G01N 31/00
[52] U.S. Cl. .................. 422/64; 422/65; 422/102
[58] Field of Search .................. 422/102, 64, 65

[56] References Cited

U.S. PATENT DOCUMENTS

| | | | |
|---|---|---|---|
| 3,992,158 | 11/1976 | Przybylowicz et al. | 422/57 |
| 4,151,931 | 5/1979 | Scherer et al. | 221/226 |
| 4,187,077 | 2/1980 | Covington et al. | 422/63 |
| 4,190,420 | 2/1980 | Covington et al. | 422/63 |
| 4,279,861 | 7/1981 | Jessop | 422/67 |
| 4,292,272 | 9/1981 | Kitajima et al. | 422/57 |
| 4,296,069 | 10/1981 | Smith et al. | 422/64 |
| 4,477,575 | 10/1984 | Vogel et al. | 436/170 |
| 4,568,519 | 2/1986 | Hamilton | 422/64 |
| 4,855,109 | 8/1989 | Muraishi et al. | 422/63 |
| 5,053,198 | 10/1991 | Quenin | 422/64 |
| 5,075,079 | 12/1991 | Kerr et al. | 422/64 |
| 5,154,889 | 10/1992 | Muraishi | 422/65 |

FOREIGN PATENT DOCUMENTS

| | | |
|---|---|---|
| 0064691 | 11/1982 | European Pat. Off. . |
| 0304838 | 3/1989 | European Pat. Off. . |
| 60-55263 | 3/1985 | Japan . |
| 60-55264 | 7/1985 | Japan . |

*Primary Examiner*—Robert J. Warden
*Assistant Examiner*—N. Bhat
*Attorney, Agent, or Firm*—McAulay Fisher Nissen Goldberg & Kiel

[57] ABSTRACT

A cartridge for storing a plurality of stacked chips having an exit for taking out the end dry analytical film chip one by one which are pushed toward the exit, and a flexible engager for inhibiting the discharge of the end chip. The exit and the engager are provided at an end portion of a side wall of the casing, the opening being provided at an end of the casing, and the flexible engager has a strength capable of releasing the end chip from the conveyor but is also capable of holding the second end, wherein the exit and the engager are provided at an end portion of a side wall of the casing, the opening being provided at an end of the casing. The engager is capable of holding the second end chip, or wherein the exit and the engager are provided at an end portion of the casing, and the engager is a non-flexible engager for releasing the end chip by its deformation occurring by the pull of the conveyor through the second end through the release of the lowermost end chip, and the exit also functions as the opening. The cartridge has a compact size and ejects only one chip while preventing the simultaneous ejection of two chips.

23 Claims, 20 Drawing Sheets

FIG. 5
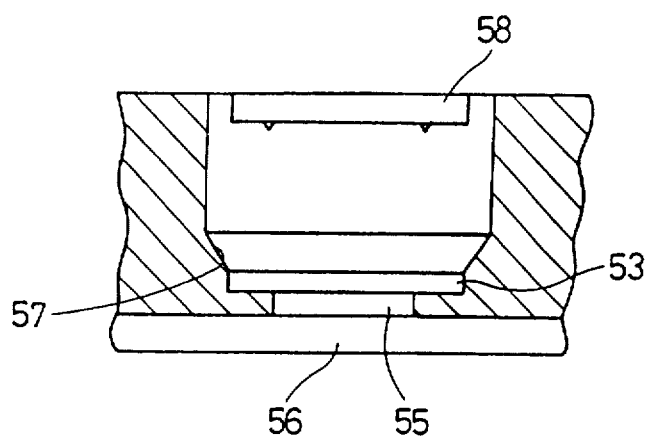
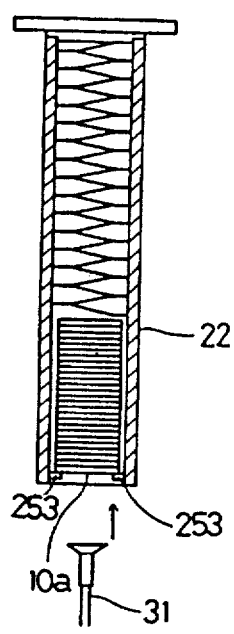
FIG. 6(a)
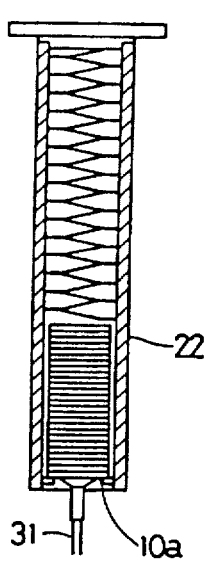
FIG. 6(b)
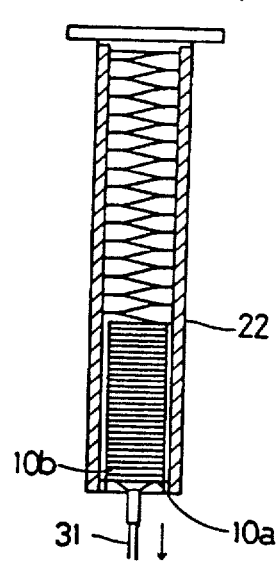
FIG. 6(c)
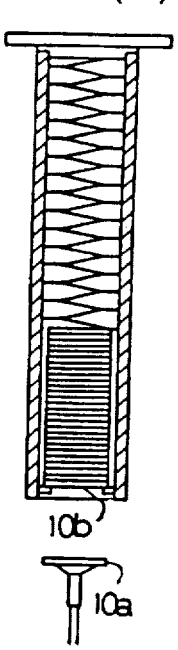
FIG. 6(d)

FIG. 27
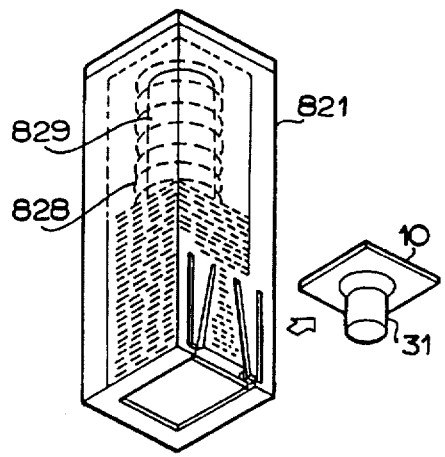
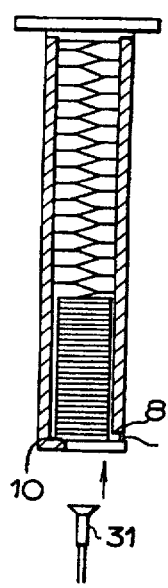
FIG. 28(A)
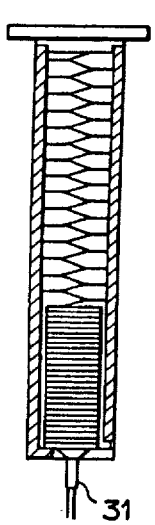
FIG. 28(B)
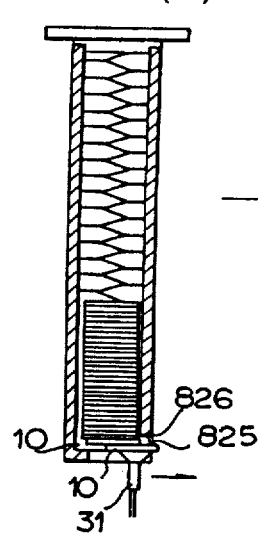
FIG. 28(C)
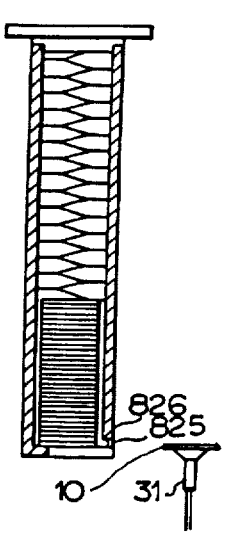
FIG. 28(D)

FIG. 33
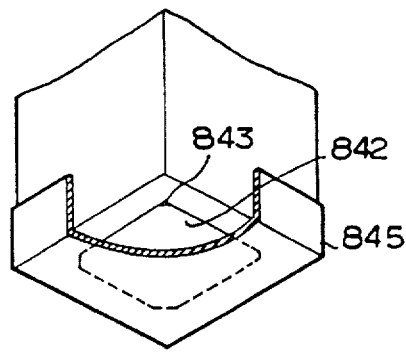
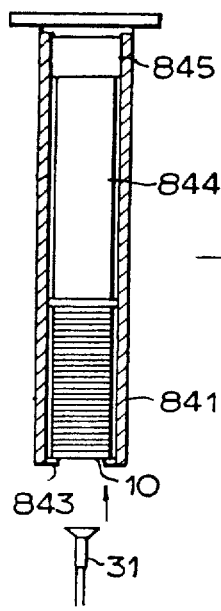
FIG. 34(A)
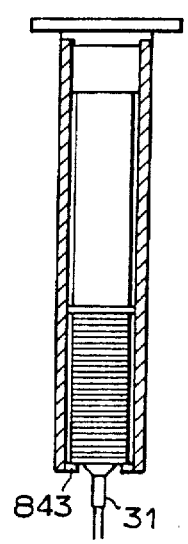
FIG. 34(B)
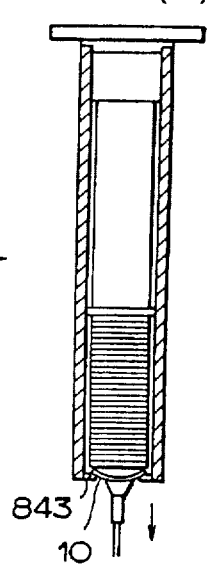
FIG. 34(C)
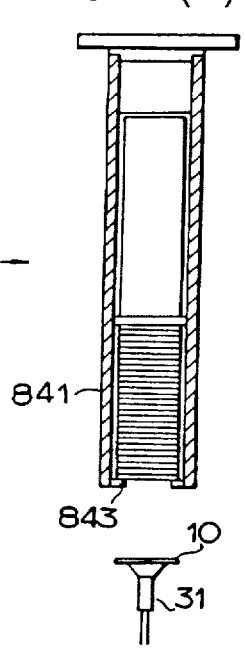
FIG. 34(D)

FIG. 35
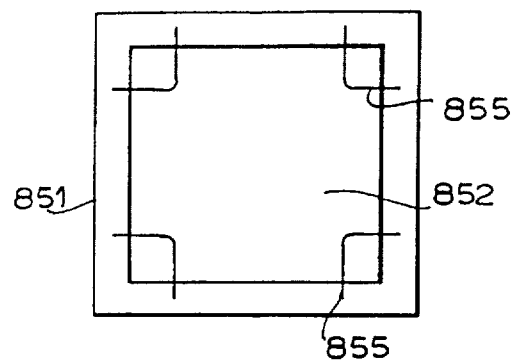
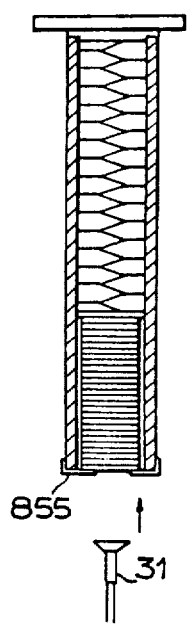
FIG. 36(A)
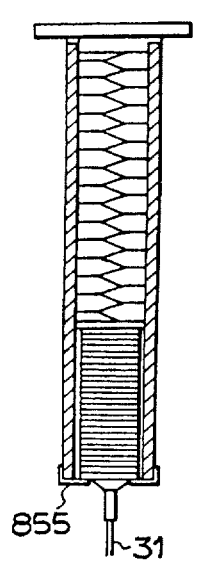
FIG. 36(B)
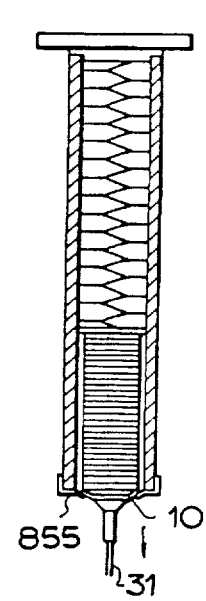
FIG. 36(C)
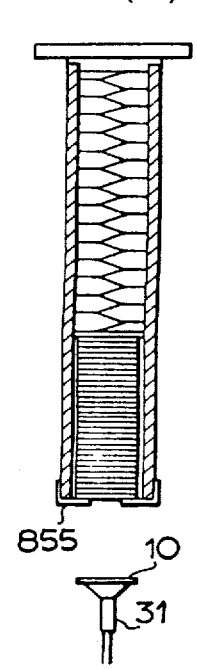
FIG. 36(D)

865  ↑
    ‾31

865  ‾31

865  10  ↓
        ‾31

865  10
     ‾31

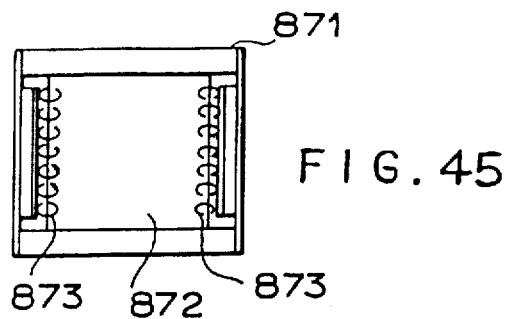
FIG. 45
FIG. 46
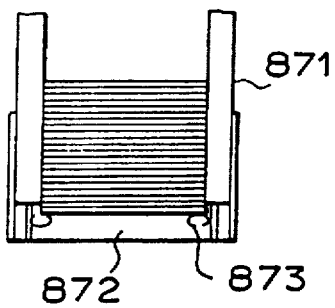
FIG. 47
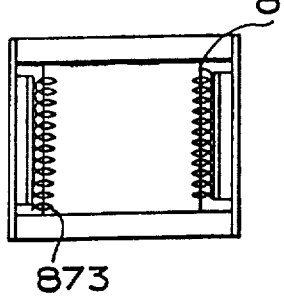
FIG. 48
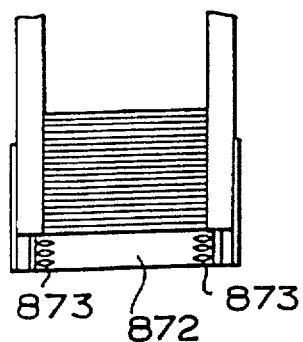

CARTRIDGE FOR STORING DRY ANALYTICAL FILM CHIPS

BACKGROUND OF THE INVENTION

This invention relates to cartridges (also called containers) for storing dry analytical film chips which are small pieces of dry analytical film cut into a specific form, such as square, rectangle, circle or ellipsoid. The dry analytical film has a reagent layer wherein chemical reaction, biochemical reaction or immunological reaction occurs with a predetermined biochemical substance (hereinafter referred to as analyte) contained in a sample solution, such as blood or urine to produce an optical density change.

In general, to analyze qualitatively or quantitatively a specific component or an activity of a specific component in a sample solution is conducted in various industrial fields. Particularly, it is very important to analyze quantitatively the content or activity of a biochemical component or the content of a solid component of a body fluid, such as blood or urine, of an organism.

Recently, various dry integral multilayer analytical films (also called multilayer analytical element) have been developed which can determine the content or activity of a specific chemical component or the content of a specific solid component by merely spotting a small drop of a sample solution (U.S. Pat. Nos. 3,992,158, 4,292,272, etc.), and put to practical use. Filter paper-type test pieces and modifications thereof composed of single layer or multilayer were also proposed (U.S. Pat. No. 4,477,575), and are, in part, put to practical use. Since a sample solution can be analyzed simply and rapidly by using the dry analytical films compared with conventional wet analysis, to use the dry analytical films is particularly desirable for a medical organization or laboratory where a great number of sample solutions is analyzed.

As a method of analyzing a chemical component of a sample solution quantitatively by using the dry analytical film, the sample solution was spotted onto the dry analytical film (when there is a spreading layer, onto the spreading layer, on the other hand, when there is no spreading layer, onto the reagent layer directly), and is kept at a fixed temperature (incubated) for a predetermined period in an incubator (thermostatic oven) to induce a coloring reaction (dye-forming reaction). Subsequently, light for measurement containing a wavelength, which has been previously selected by the combination of a predetermined biochemical substance in a sample solution and a reagent contained in a dry analytical film, is irradiated to the dry analytical film, is irradiated to the dry analytical film, and the optical density is measured. The concentration or activity of the biochemical substance in the sample solution is determined by applying the optical density to a calibration curve indicating the correlation between the optical density and the concentration or activity of the biochemical substance which has been previously determined.

The above dry analytical film is composed of at least one layer of a reagent layer provided on a support formed of organic polymer, preferably further a spreading layer provided on the upper side of the reagent layer. The dry analytical film is formed into a chip, and put in a slide frame made of organic polymer (called chemical analytical slide) in order to treat by automatic operation. The slide frame also functions to keep the dry analytical film flat which tends to warp in dry conditions.

Incidentally, reagents in the reagent layer do not react, unless moisture is present. However, there is a possibility to start reaction at the moment to absorb moisture. Accordingly, the reagent layer must be kept in dry conditions until measurement is conducted. However, as mentioned above, the dry analytical film chip warps in dry conditions, and then, the dry analytical film chip is forced to be flat by placing in the slide frame. Moreover, although a part of the dry analytical film mounted in a slide frame is exposed at the opening of the upper slide frame to which a liquid sample is spotted, the exposed part (the upper surface of the spreading layer or reagent layer) of the dry analytical film is present at the bottom of an indentation formed by the thickness (in general, about 200 µm to 1 mm) of the opening part of the upper slide frame. By the indentation structure, the upper surface of the dry analytical film mounted in the slide frame onto which a liquid sample is spotted is protected from damage and contamination.

As a cartridge for storing chemical analytical slides formed of a dry analytical film and a slide frame and protecting from moisture, Japanese Patent KOKAI Nos. 60-55263 and 60-55264 disclose a cartridge which is provided with an opening for ejecting the slides on one wall contacting an end panel of the cartridge and a flexible cover capable of closing the opening provisionally on the front of the opening parallel to the wall. As mentioned previously, the dry analytical film is necessary to be protected from moisture so as not to absorb moisture prior to use, and the flexible cover covers entirely the opening for ejecting the analytical slide because the main function of the cartridge is to protect the dry analytical films placed therein from moisture. Accordingly, the whole upper surface of the analytical slide is rubbed by the lower end of the flexible cover urged downwardly by the elasticity of the cover at the time of ejecting from the inside of the cartridge. The chemical analytical slide wherein the dry analytical film is placed in the slide frame is not damaged nor contaminated through rubbing by the cover, even in the case of the cover having the above structure.

However, analyzers using the above chemical analytical slides tend to be a big apparatus. That is, in a big medical organization, since a great quantity of chemical analytical slides is expended in a short period, a large size cartridge is used. Moreover, it is necessary to provide the number of cartridges corresponding to the number of the biochemical substances to be analyzed (analyte), and thereby, the space for setting the cartridge becomes great.

Besides, the cost of the slide frame is great to elevate the cost of chemical analytical slide, and the presence of the slide frame itself increases the size of cartridges and incubator.

Thereupon, the inventors developed several kinds of cartridges and incubator wherein dry analytical film chips can be used as it is (without mounted in a slide frame), and thereby, the cartridges can be made compact (Japanese Patent Application Nos. 4-5508, 4-16098).

In the cartridges, dry analytical film chips are stacked in the state that the support portion is positioned on the upper side, and each analytical film chip is taken out of the cartridge by sucking the support portion by a suction pad. Thereafter, the suction by the suction pad is changed over to the spreading layer or reagent layer portion, the film chip is turned, and conveyed to the incubator in the state that the spreading layer or reagent layer is positioned on the upper side. As a result, the conveying mechanism from the cartridge to the incubator is complex. Moreover, since the spreading layer and the reagent layer cannot be strongly sucked by the suction pad, troubles occurred due to the insufficient suction force, and carry-over by the suction pad sucking the spreading layer or reagent layer also occurred.

SUMMARY OF THE INVENTION

An object of the invention is to provide a cartridge capable of ejecting surely one dry analytical film chip (preventing from simultaneous two chips ejection) with a simple structure keeping a compact size.

Another object of the invention is to provide a method of conveying dry analytical film chips in a simple process surely and safely from a cartridge to an incubator and to provide a cartridge therefor.

The present invention provides a cartridge for storing dry analytical film chips which has achieved the above object, which comprises,

- a casing wherein a plurality of the dry analytical film chips having at least one reagent layer provided on a support are stacked,
- an exit for taking out the end dry analytical film chip of the stack one by one,
- an urging means for pushing the dry analytical film chip stack toward the exit,
- an engaging means for inhibiting (or stopping) the discharging of the end dry analytical film chip of the stack from the casing, and
- an opening for passing the conveying means of the dry analytical to be taken out,
- wherein the exit and the engaging means for inhibiting the discharge of the last or lowermost dry analytical film chip are provided at an end portion of a side wall of the casing,
- the opening is provided at the bottom of the casing, and
- the engaging means for inhibiting the discharge of the last or lowermost dry analytical film chip is a flexible engaging means having a strength capable of releasing the lowermost dry analytical film chip by the conveying means but capable of holding the second from the last or lowermost dry analytical film chip.

Another cartridge for storing dry analytical film chips which has also achieved the above object is, in the above cartridge,

- the exit and the engaging means for inhibiting the discharge of the last or lowermost dry analytical film chip are provided at an end portion of a side wall of the casing,
- the opening is provided at the bottom of the casing, and
- the engaging means for inhibiting the discharge of the end dry analytical film chip is a flexible engaging means for the end film chip having a strength capable of releasing the last or lowermost dry analytical film chip by the conveying means, and an engaging means capable of holding the second from the last or lowermost dry analytical film chip is further provided.

Another cartridge for storing dry analytical has also achieved the above object is, in the film chips which comprises, above cartridge,

- the exit and the engaging means for inhibiting the discharge of the last or lowermost dry analytical film chip are provided at an end portion of the casing, and
- the engaging means for inhibiting the discharge of the last or lowermost dry analytical film chip is a flexible or non-flexible engaging means having a size capable of releasing the last or lowermost dry analytical film chip by its deformation occurring by the pull of the conveying means but capable of holding the second from the last or lowermost dry analytical film chip through the release of the last or lowermost dry analytical film chip, and the exit also functions as to opening.

The above object has also been achieved by a method of conveying dry analytical film chips which comprises,

- taking out one dry analytical film chip having at least one reagent layer provided on a support in a state that the support is positioned on the underside from the lower end portion of a dry analytical film cartridge wherein a plurality of the dry analytical film chips are stacked in the state that the support is positioned on the underside by a conveying means, and
- conveying the dry analytical film chip taking out in the state that the support is positioned on the underside as it is to a dry analytical film chip placing portion of an incubator by said conveying means.

BRIEF DESCRIPTION OF THE DRAWINGS

FIG. 5 is a partial longitudinal sectional view thereof.

FIG. 6(a), 6(b), 6(c) and 6(d) illustrate a procedure of taking out one dry analytical film chip from the cartridge. FIGS. 6(a), 6(b), 6(c) and 6(d) show the individual sequential steps.

FIGS. 6(a), 6(b), 6(c) and 6(d) show the individual sequential steps in the procedure of removing one dry chip from the cartridge.

FIGS. 20 through 22 are partial enlarged front views of respective flexible engaging means which are modifications of the flexible engaging means used in FIGS. 16 through 18.

FIG. 27 is a perspective view of the cartridge of FIG. 23 viewed from the underside.

FIGS. 28(A), 28(B), 29(C) and 28(D) illustrate a procedure of taking out one dry analytical film chip from the cartridge of FIG. 23. FIGS. 28(A), 28(B), 29(C) and 28(D) as the individual FIGS. 19(A), 19(B), 19(C) and 19(D) also illustrate the same type of sequential steps.

FIG. 33 is a perspective view of the lower part in the state of not use.

FIGS. 34(A), 34(B), 34(C) and 34(D) illustrate a procedure of taking out one dry analytical film chip from the cartridge of FIG. 30. FIGS. 34(A), 34(B), 34(C) and 34(D) in the same manner as FIGS. 19(A), 19(B), 19(C) and 19(D) respectively illustrate the sequential steps.

FIG. 35 is a bottom view of another cartridge for storing dry analytical film chips embodying the invention.

FIGS. 36(A), 36(B), 36(C) and 36(D) illustrate a procedure of taking out one dry analytical film chip from the cartridge of FIG. 35. FIGS. 36(A), 36(B), 36(C) and 36(D) also respectively illustrate the sequential steps in a manner similar to FIGS. 19(A), 19(B), 19(C) and 19(D).

FIG. 45 is a bottom view of another cartridge for storing dry analytical film chips embodying the invention, and FIG. 46 is a sectional view of the lower part thereof.

FIG. 47 is a bottom view of a modification of the cartridge of FIG. 45 wherein a plurality of loop rows of a hook-and-loop fastener, and FIG. 48 is a sectional view of the lower part thereof.

Figure 1:
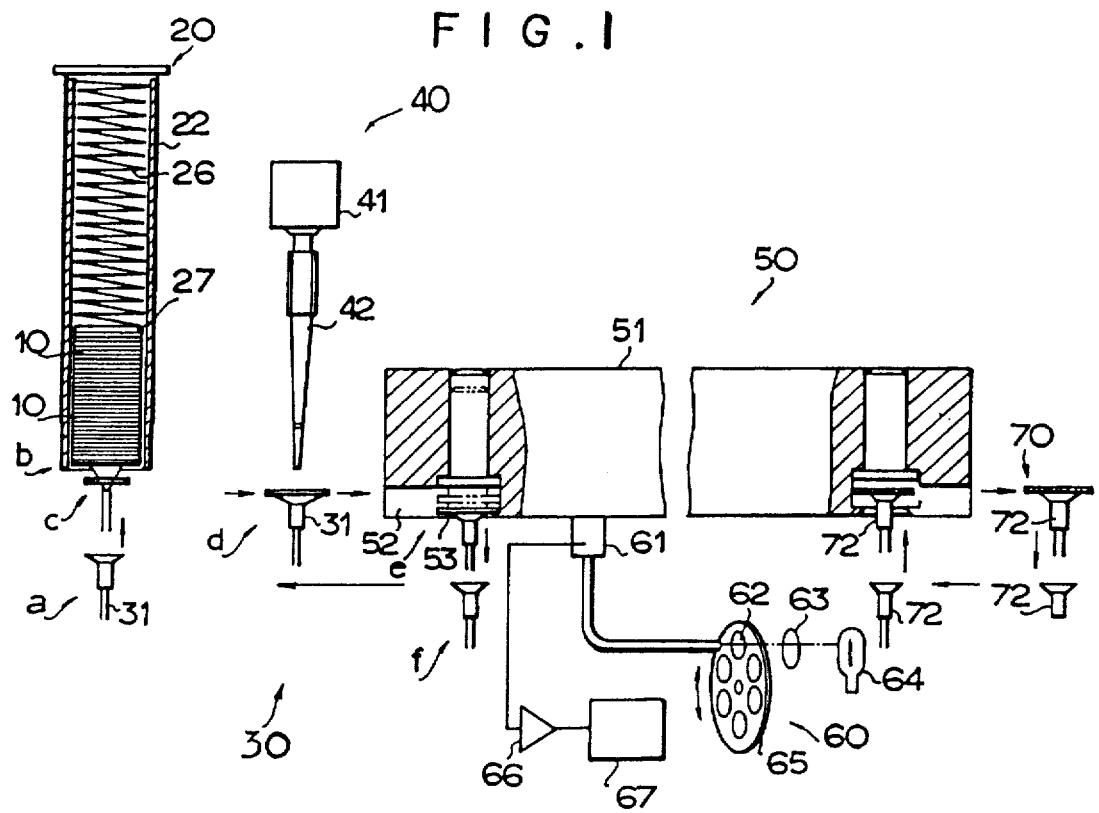
FIG. 1 is a schematic side view of an analyzer for conducting the method of conveying dry analytical film chips of the invention with partial sections.

In the figures, the elements are designated by the following numerals:

10 . . . Dry analytical film chip
11 . . . Support
12 . . . Reagent layer
13 . . . Spreading layer
20 . . . Dry analytical film chip storing portion
21 . . . Cartridge placing portion
22 . . . Cartridge Casing
24 . . . Exit Opening
251 . . . Notch
252 . . . Holding part
253 . . . Engaging urging means for engaging dry analytical film chip (engaging spring)
26 . . . Urging means for pushing dry analytical film chip toward the opening (coil spring)
30 . . . Dry analytical film chip conveying portion
31 . . . Conveying means (suction pad)
40 . . . Spotting portion
50 . . . Incubation
53 . . . Placing part
60 . . . Photometric portion
70 . . . Discharging portion
80 . . . Cartridge
212,822 . . . Exit
814 . . . Flexible engaging means
825 . . . Flexible engaging means for the lowermost film chip
842,852,862,872 . . . Opening for discharge
843 . . . Non-flexible engaging means
855 . . . Flexible engaging means
865 . . . Edge side non-flexible engaging means
873 . . . Loops of hook-and-loop fastener

DETAILED DESCRIPTION OF THE INVENTION

In the method of conveying dry analytical film chips, it is sufficient that the dry analytical film chip can be taken out from the cartridge in the state that the support is positioned on the underside, and the cartridge of the dry analytical film chip, the taking out method and the like are not limited. As to conveying, it is sufficient that the dry analytical film chip can be conveyed in the state that the support is positioned on the underside, and the incubator, the conveying method and the like are not limited. For example, as the conveying means, there are the means that the dry analytical film chip is conveyed in the state of being fixed by a suction pad, the means that the dry analytical film chip is conveyed in the state of nipping the side edges opposite to each other mechanically, and the like.

Since the dry analytical film chip is conveyed in the state that the spreading layer or the reagent layer is positioned on the upper side, a sample solution can be spotted during conveying.

The dry analytical film has a support and at least one reagent layer, and preferably a spreading layer, in this order.

The support is composed of a sheet of organic polymer, such as PET (polyethylene terephthalate) or polystyrene, and is preferably light-transmissive. The support functions to keep the dry analytical film chip flat. A reinforcing sheet may be laminated under the support in order to improve the function to keep flat. The reinforcing sheet may be made of the same organic polymer as the support or other polymer preferably having a greater rigidity. The reinforcing sheet is preferably light-transmissive and thicker than the support. The form and size of the reinforcing sheet may be any one capable of keeping the dry analytical film chip flat. Applicable forms are a square, rectangle, circle and the like, and it is usually similar to the form of the dry analytical film chip. The size may be smaller than, larger than or equal to the dry analytical film chip. When the reinforcing sheet is formed so as to project from the dry analytical film chip, the film chip can be conveyed by nipping the projected portion. As a means for making the reinforcing sheet to transmit the measuring light, the reinforcing sheet is formed of a light-transmissive material. Such a material includes polyethylene terephthalate (PET), polystyrene, acrylic resin represented by polymethyl methacrylate. Another means is to form a light-transmissive hole at the position where measuring light passes. The form of the hole may be a circle, ellipsoid, square, rectangle or the like.

The reagent layer is composed of reagent components necessary for the coloring (dye-producing) or discoloring reaction for detecting an analyte (the object biochemical component to be determined) and a hydrophilic polymer binder, such as gelatin, polyacrylamide or polyvinyl alcohol. The reagent layer does not always require the reagent components, such as the dry analytical film for the determination of hemoglobin.

The dry analytical film applicable to the invention also includes test elements in filter paper type and modifications thereof in a single layer or multilayer. The test elements are laminated to the aforementioned support or reinforcing sheet prior to use.

The form of the dry analytical film chip is, in general, a square, rectangle, circle, ellipsoid or the like, having a side of about 8 to 20 mm in the case of square and rectangle, a diameter (both of the major axis and the minor axis) of about 8 to 20 mm in the case of circle and ellipsoid, and the thickness is about 300 μm to 1.5 mm. In view of analytical operation and manufacture, square and rectangle near square are preferred.

As the biological components analyzable by the dry analytical film, there are blood sugar (glucose), cholesterol, urea nitrogen (BUN), creatinine, bilirubin, glutamic-oxaloacetic transaminase (GOT), glutamic-pyruvic transaminase (GPT), amylase, c-reactive protein (CRP), and the like.

The casing of the cartridge is the cartridge body, and has a space for loading the dry analytical film chips, an exit for taking out the dry analytical film chip, an urging means for pushing the dry analytical film chip stack toward the exit, an engaging means for inhibiting the discharge of the lowermost dry analytical film chip in the casing, and an opening for passing the conveying means of the dry analytical film chip to be taken out.

The form and size of the casing are designed according the form and size of the dry analytical film chip to be loaded. The stacking form is not limited to vertical stacking but may be oblique stacking. The support portion of the dry analytical film chip may be faced irrespective of upward or downward. It is preferable to form longitudinal ribs on the inner walls of the casing in order to render the movement of the dry analytical film chips smooth in the casing.

The urging means is, in general, provided in the space between the top of the casing and the uppermost dry analytical film chip in the loaded stack. Suitable urging means are a coil spring, folded leaf spring, weight, drying agent package having weight action or the like can be used as the urging means.

A further example of the urging means is composed of providing a vertical positioning means, such as ratchet teeth, on two inner wall surfaces facing each other of the casing, and providing a means (for example, a pair of pawls) for preventing return motion (upward) engaged with the vertical positioning means on the push plate. The urging means can be constructed by referring to U.S. Pat. No. 4,151,931. This urging means is preferable for the cartridge wherein the exit for taking out the dry analytical film chip is formed at the upper part.

It is preferable to provide a push plate between the urging means and the uppermost dry analytical film chip so as not to damage the uppermost film chip and to push uniformly.

The form and size of the push plate is not limited but is usually similar to the dry analytical film chip. The surface of the push plate on the side contacting the dry analytical film chip is formed of an inactive material so as not to affect the spreading layer and the reagent layer adversely. For example, the surface is a mirror face made of stainless steel or plated with chrome or a non-adsorptive surface coated by a non-adsorptive material such as polytetrafluoroethylene. A penetrated hole may be formed at the center of the push plate so as not to be adsorbed by the suction pad.

It is also preferable to provide a means for preventing a part of the loaded dry analytical film chips from becoming vertical by the drop shock of the cartridge. Such a means includes a holding bar inserted into the coil spring, a cushioning material filling the space between the top of the casing of the upper face of the weight, and the like. The size of the weight itself may be formed so as to be consistent with the space. Another means is to mount a leaf spring on the side of the push plate opposite to the side contacting the dry analytical film chip, to form ribs on the inner walls of the casing in the vertical direction with which the leaf spring is engaged.

In the cartridge of the invention, the following embodiments can be taken concerning the exit for taking out the dry analytical film chip, the engaging means for inhibiting the discharge of the lowermost dry analytical film chip in the casing, and the opening for passing a conveying means of the dry analytical film chip for taking out.

In an aspect of the invention, the exit is provided at the bottom of the casing, and also functions as the opening. In this case, the dry analytical film chip is taken out vertically, and the exit has a size greater than the size of the dry analytical film chip. The exit is usually cut at a right angle, but may be cut obliquely at an angle of less than 30 degrees with the right angle direction.

The engaging means holds the stack of the dry analytical film chip (usually 100 sheets at the maximum) in the cartridge resisting the pushing force of the urging means and the weight of the dry analytical film chip stack. When the lowermost dry analytical film chip is taken out by the conveying means, the engagement of the dry analytical film chip with the engaging means is released by utilizing the deformation of the film chip, and in the case of flexible engaging means, as well as the deformation of the flexible engaging means, and the dry analytical film chip can be taken out of the cartridge through the exit.

The engaging means is provided at facing two or four corners or facing two or four sides of the exit. The engaging end of the engaging means is projected toward the inside of the casing preferably in the range of about 0.5 to 3 mm from the inner wall or the extension thereof. The form of the engaging means may be a plate, beam, bar, wire or the like. The form of the plate is a triangle, rectangle or the like and the beam and the bar span the corner of the exit or the like. The wire can be used in a form of U-letter. When the engaging means is formed into beam plate, corners to contact the dry analytical film chip are preferably rounded so as to facilite passing the film chip therethrough and not to damage it.

The engaging means can be fixed by embedding, screwing, riveting, welding, adhering using an adhesive, or integral molding together with the casing.

The engaging means may be flexible, non-flexible or combination thereof.

The flexible engaging means is formed of a sheet of a hard polymer, such as polyethylene terephthalate (PET), polypropylene, hard polyethylene, polystyrene, polamide (nylon), polyvinyl chloride or polyvinylidene chloride. As to the rigidity of the hard polymer sheet, for example in the case of a PET sheet, a preferable rigidity is in the range corresponding to the rigidity of a non-crystalline PET sheet about 80 to 120 μm in thickness.

The engaging means may be an engaging urging means which is an elastic body (spring) formed of the same material as the cartridge or an organic polymer having strong flexibility (elasticity) or a spring formed of metal. The form of the engaging urging means is, for example in the case of leaf spring, a claw or a narrow plate gently curled toward the inside of the cartridge, and in the case of wire spring, gently curled toward the inside of the cartridge or bent into U-form.

One or more rows of elastic single fiber loops, straight or brush-formed elastic single fibers or straight or brush-formed elastic plural fiber twist yarns can be used as the flexible engaging means. A suitable number of the rows is 1 to 4, preferably 2 to 3. The top of the brush-formed single fibers is preferably rounded or formed into a ball having a diameter greater than the thickness of the fiber. In the case of the yarn, the top of each fiber is preferably rounded. The loops of a hook-and-loop fastener can be used as the elastic single fiber loops. The loops and brush-formed fibers and yarns are preferably arranged so as to be absent or less at the part corresponding to the central part of the side end of the dry analytical film chip (the spreading region or the diffusion region in the planar direction (lateral directions) of the liquid sample spotted). The distance between the lower end of the loop or fiber or yarn and the underside of the exit, the maximum width and the length are similar to the case of the engaging tongue portion described later.

The non-flexible (rigid) engaging means is formed of a hard polymer, such as polyethylene terephthalate (PET), polypropylene, hard polyethylene, polystyrene, polyamide (nylon), polyvinyl chloride or polyvinylidene chloride, metal, such as thin stainless steel or brass.

In order to take out only one dry analytical film chip more surely, a notch may be formed on a side of the exit and a holding part is provided on the opposite side. The notch has a size capable of entering only the lowermost dry analytical film chip, and the second lowermost one is stopped by the wall of the casing. The holding part has substantially no elasticity, and surely holds the stack of the dry analytical film chips urged downward. The holding part is preferably composed of a plate-formed slender metal piece embedded in or screwed to the side of the exit, a plate-formed slender projection integrally molded with the casing, or the like. The projected length of the holding part toward the inside of the cartridge is about 1 to 3 mm, and the width is from about 5 mm to the same length as the side. The notch may be provided on both facing sides of the exit.

In another aspect of the invention, the exit for taking out the dry analytical film chip and the engaging means for inhibiting the discharge of the lowermost dry analytical film chip in the casing are provided at the lower end portion (including the vicinity of the lower end) of a side wall of the casing, and the opening for passing a conveying means of the dry analytical film chip for taking out is provided at the bottom of the casing.

The exit has a size capable of passing the dry analytical film chip laterally, and formed generally in the horizontal direction. The exit is usually one, but may be formed on two facing or adjacent sides. By forming two exits as above, it is possible to take out in two directions.

The engaging means is a flexible engaging means, and provided in the direction parallel to the wall, i.e. the direction of the extension of the wall. The flexible engaging means has a strength capable of releasing the lowermost dry analytical film chip fixed and conveyed by the conveying means and slid along the bottom end panel with bending in the direction parallel to the bottom end panel, but capable of holding the second lowermost dry analytical film chip in contact with the sliding lowermost film chip. The form of the flexible engaging means may be anyone exercising the above action, but an inverted U form and II form are preferred. In both forms, a pair of the projections (engaging tongue portions) downward act substantially as the engaging means, and the engaging tongue portion may be in a form of tongue, long tongue, squamation, inverted triangle, wedge or the like.

The lower end of the engaging tongue portion may contact the underside of the exit, but the lower end is preferably apart from the underside at a distance of ½ to ⅔ of the dry analytical film chip thickness. As the actual numerical value, since the thinnest dry analytical film chip is about 300 μm, a preferable distance between the lower end of the engaging tongue portion and the underside of the exit is about 100 to 300 μm. A suitable width of the engaging tongue portion is in the range of about 1 to 3 mm at the maximum width, and a suitable length is about 250 μm to 3 mm. The distance between two engaging tongue portions is preferably almost the same as or wider (longer) than the maximum width of the spreading region or the diffusion region in the planar direction (lateral directions) in the spreading layer or the reagent layer which are the uppermost layer of the dry analytical film chip. However, in the case that the size of the dry analytical film chip is small, the distance may be slightly narrower (shorter) than the above maximum width of the spreading area or the diffusion area. As the actual distance, it is preferable that each engaging tongue portion is positioned about 0.5 mm to 1 mm apart from the side edge of the dry analytical film chip. In the case of the dry analytical film chip having the spreading layer, the shortest (narrowest) distance between the engaging tongue portions is about 7 mm, and in the case of the dry analytical film chip wherein the reagent layer is the uppermost layer, the shortest (narrowest) distance is about 5 mm.

The form of the lower end of the engaging tongue portion is preferably rounded without a polygonal top (irrespective of acute angle or obtuse angle). The edge portions of both sides of the engaging tongue portion are also preferably rounded (having a U-form section). The inner surface of the flexible engaging means preferably conforms to the inner surface of the casing.

The material and the fixing means of the flexible engaging means are similar to the aforementioned. The flexible engaging means may be inverted, and in this case, the above upper and lower positions are inverted.

The flexible engaging means may be composed of a flexible engaging means for the lowermost film chip and an engaging means for the second lowermost film chip is further provided.

The flexible engaging means for the lowermost film chip is provided on the wall having the exit downward parallel to the wall face, and engages the lowermost dry analytical film chip to inhibit going out of the casing. The engaging means has a flexibility capable of passing the lowermost dry analytical film chip by bending in the direction parallel to the bottom end panel at the time of discharging it by a conveying means. This flexible engaging means is different from the aforementioned one in the point that it is not necessary to keep the second lowermost dry analytical film chip trailed by the lowermost one. That is, the second lowermost dry analytical film chip is kept by the engaging means for the second lowermost film chip. Accordingly, it is sufficient that the flexible engaging means for the lowermost film chip has a rigidity capable of preventing incidental springing out of the film chip. The other constructions may be similar to the aforementioned flexible engaging means. However, the flexible engaging means for the lowermost film chip may be provided with a function capable of keeping the second lowermost dry analytical film chip like the aforementioned one. By employing such a construction, even in the case that the flexible engaging means for the second lowermost film chip cannot prevent the discharge of the second lowermost dry analytical film chip due to its thin thickness, the flexible engaging means for the lowermost film chip keeps it. Accordingly, this construction is suitable for using dry analytical film chips different in thickness.

The engaging means for the second lowermost film chip prevent the discharge of the second lowermost dry analytical film chip in contact with the lowermost dry analytical film chip when the lowermost one is discharged by a conveying means. The lower end of the engaging means for the second lowermost film chip is positioned between the upper side and the underside of the second lowermost dry analytical film chip, and has a rigidity capable of keeping it. The other constructions are not limited. For example, the engaging means is formed of the same material and integrally molded together with the casing, or it may be separately provided from the casing.

Information concerning the loaded dry analytical film chip may be indicated on the outer surface of the casing by using notches, indentation, projections, magnetic code, bar code, Karura code (code in the form of cross in square capable of indicating hexadecimally) or the like. The information may be printed by letters, such as alphabet, Japanese letters, numerals or the like capable of being read by a human being.

The cartridge is loaded with the dry analytical film chip stack, and placed in the cartridge placing portion of an analyzer. The dry analytical film chip is taken out one by one from the cartridge by a conveying means, and delivered to a spotting portion. A liquid sample is spotted onto the dry analytical film chip at the spotting portion, and delivered to an incubator. After incubating, the dry analytical film chip is measured by photometry, and discharged from the incubator.

In the cartridge of the invention, since dry analytical film chips not placed in a frame are loaded, and nevertheless the film chips can be taken out one by one successively one by one at the time of conductive a biochemical assay or immunological assay, the size can be sharply smaller than the conventional cartridge for loading chemical analytical slides wherein each dry analytical film chip is placed in a frame. As a result, biochemical analyzer and immunological analyzer can be made compact due to the decrease in the setting space for the cartridges. Since the frame is not used, the cost for frame can be omitted. Although the dry analytical film chip cartridges are stocked in a dehumidified container, since only the dry analytical film chips are stocked, dehumidification efficiency can be improved. Furthermore, since the dry analytical film chip itself is very small and light compared with the chemical analytical slide, the loaded dry analytical film chips can be urged easily only by the urging means, such as a spring, provided in the casing without utilizing an outer boosting member like the conventional cartridge. As a result, the mechanism of the cartridge can be simplified.

In the method of conveying the dry analytical film chips using the cartridge of the invention, since the dry analytical film chips are conveyed facing the spreading layer or the reagent lay upward, the conveying is conducted under very simple mechanism. Since the conveying mechanism do not touch the spreading layer or the reagent layer through conveying, the dry analytical film chips can be conveyed safely and surely without the occurrence of contamination and carry-over problem.

EXAMPLES

Example 1

An example of the method of conveying dry analytical film chips and a cartridge for storing them are illustrated in FIGS. 1 through 15.

Figure 15:
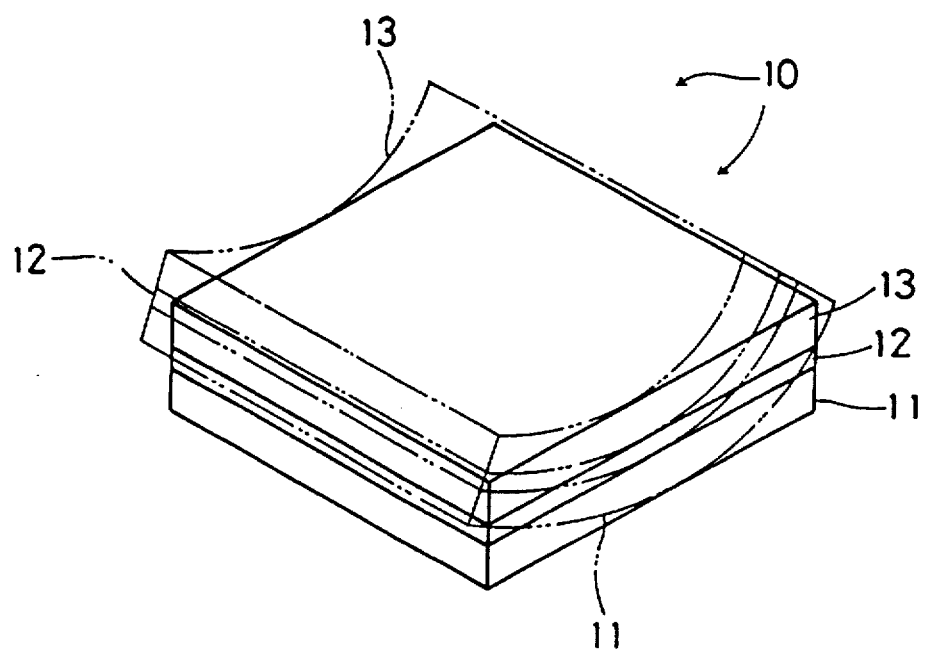
FIG. 15 is a perspective view of a dry analytical film chip used in the invention.

A representative form of the dry analytical film chip 10 used in the invention is square or rectangle near square as shown in FIG. 15, and the length of a side is in the range of about 10 mm to about 20 mm and the thickness is in the range of about 0.4 mm to about 1.5 mm. The dry analytical film chip of FIG. 15 is a square having a size of 15 mm×15 mm×0.5 mm (thickness), and composed of a support 11 made of PET (polyethylene terephthalate) or polystyrene, a reagent layer 12 provided on the support 11 and a spreading layer 13 provided further thereon. The dry analytical film chip 10 is usually more or less warped (or bent) curved as indicated by a two-dot chain line in FIG. 15 rendering the spreading layer inside in dry conditions prior to use.

Figure 2:
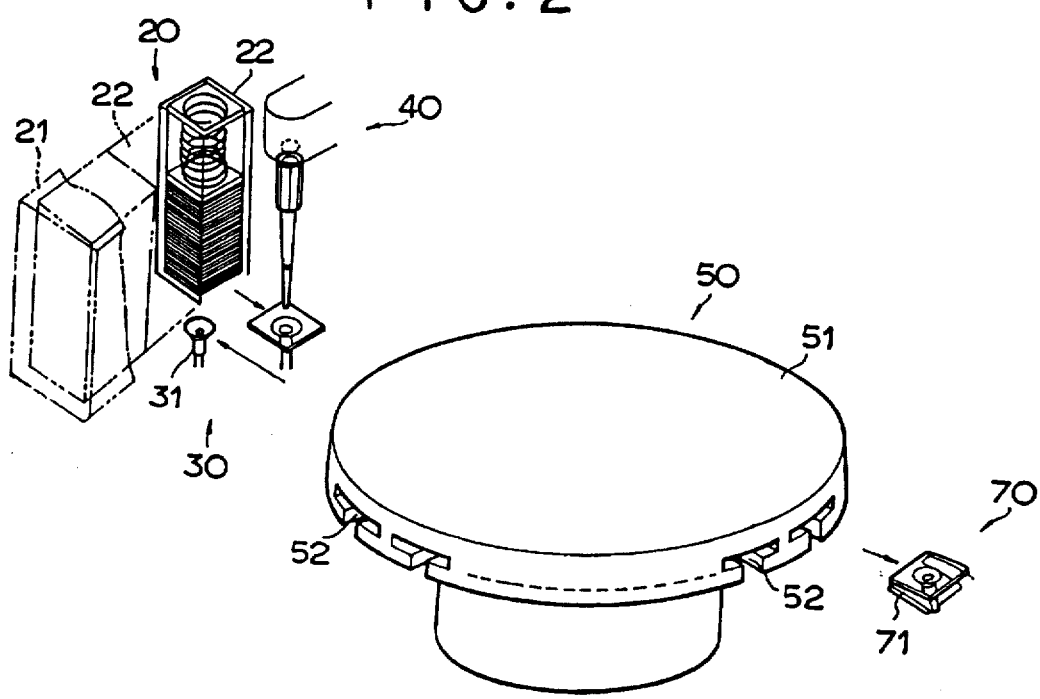
FIG. 2 is a schematic perspective view of the above analyzer.

The analyzer for conducting the method of conveying dry analytical film chips of the invention is, as shown in FIGS. 1 and 2, provided with a dry analytical film chip storing portion 20 for storing virgin dry analytical film chips 10, a dry analytical film chip conveying portion 30 for taking out the dry analytical chips 10 from the storing portion 20 and delivering to the incubator described below, a spotting portion 40 for spotting a sample liquid onto the dry analytical film chip 10 during conveying in the conveying portion 30, an incubator 50 for keeping the dry analytical chemical film chip 10 onto which the sample liquid has been spotted at a constant temperature for a predetermined time, a photometric portion 60 for measuring the reflection optical density of the dry analytical film chip 10 wherein a coloring reaction has occurred in the incubator 50, and a discharge portion 70 of the dry analytical film chip for discharging the dry analytical film chip 10 which has been measured at the photometric portion 60 from the incubator 50.

The dry analytical film chip storing portion 20 is provided with a box which is used as the cartridge placing portion 21, and the number of the dry analytical film chip cartridges 22, . . . , 22 corresponding to the number of the kinds of analytes are loaded in the box 21.

Figure 3:
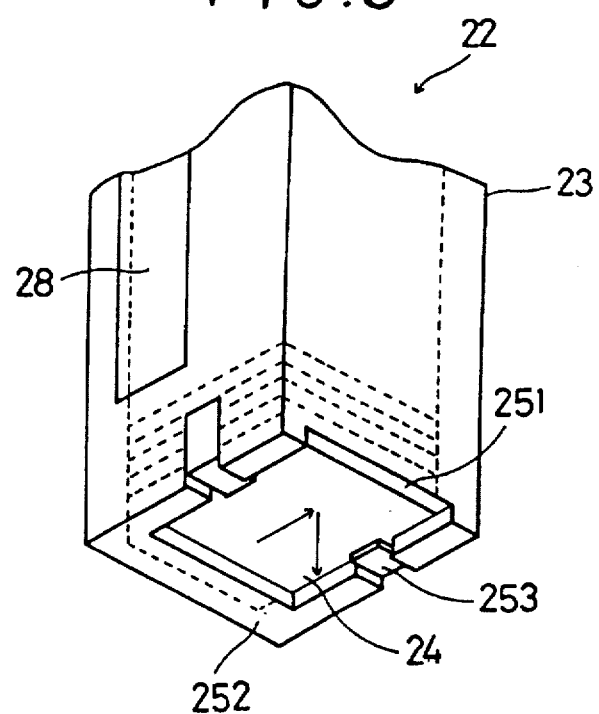
FIG. 3 is a partial perspective view of the lower part of a cartridge for storing dry analytical film chips embodying the invention viewed from the underside.

The dry analytical film chip cartridge 22 is, as shown in FIG. 3, composed of a casing 23 in a form of hollow rectangular parallelepiped having an outer size of about 18 mm×18 mm×100 mm and a thickness of about 1 mm, and formed of an organic polymer colored black so as to have light-shielding ability. An opening 24 for taking out the dry analytical film chip 10 is formed at the lower part of the casing 23. The casing 23 is further provided at the sides surrounding the opening 24 with a shallow rectangular notch 251 so that the lowermost film chip is slidable outward in the lateral direction by about 2 mm to about 3 mm, a holding part 252 provided on the side opposite to the notched side, a pair of engaging urging means (engaging spring) 253 on the other facing sides mounted in a state that the front end is projected into the opening 24. As shown in FIG. 1, a coil spring 26 for pushing the dry analytical film chips 10 downward is fixed to the reverse side of the top of the casing 23, and a push plate 27 having a similar size to the dry analytical film chip 10 is fixed to the lower end of the coil spring 26.

Each engaging spring 253 is set so as to have a strength capable of still holding the stack of the dry analytical film chips 10 by engaging the lowermost one, even when the urging force of the coil spring 26 is at the maximum, i.e. the loaded amount of the dry analytical film chips 10 is at the maximum, and on the other hand, capable of releasing the lowermost dry analytical film chip 10, when the lowermost one is sucked by the suction pad described later and pulled downward. The engaging spring 253 is an elastic body made of the same material as the cartridge or an organic polymer having a strong elasticity, and is an elastic projection (claw projection) in a form of a narrow plate gently curved toward the inside of the cartridge.

The holding part 252 provided at the end opposite to the notch 251 has substantially no elasticity (spring action), and acts to hold surely the stack of the dry analytical film chips urged downward. The holding part 252 is formed of a slender plate projection integrally molded together with the cartridge. The length of the holding part 252 projected toward the inside of the cartridge is in the range of about 1 to 3 mm, and the width is in the range from about 5 mm to the same length as the side.

When the dry analytical film chip 10 is taken out from the opening 24 of the cartridge, the underside of the support (substrate) of the analytical film chip 10 is sucked by the suction pad 31 to fix it. Then, the fixed film chip 10 is moved horizontally toward the notch 251 at a distance slightly longer that the projected length of the holding part 252, and thereafter, the suction pad 31 is moved downward to take out the analytical film chip 10 from the opening 24 of the cartridge opposing two engaging springs 253 (engaging claw).

A magnetic code 28 may be provided on the outer surface of the casing 23 as shown in FIG. 3. The magnetic code 28 has been recorded with various information, such as the kind of the stored dry analytical film chips 10, lot number, lot-specific information data for correction, analyte (analytical item), shelf life, and the like. This information is read by a magnetic head (not illustrated) and utilized for the biochemical analysis at a control station (not illustrated).

The dry analytical film chip cartridge 22 has the structure as above, and many dry analytical film chips 10 are loaded therein in a state that the support 11 is positioned on the underside, i.e. the spreading layer 13 (or the reagent layer 12) is positioned on the upper side. The stack of the dry analytical film chips 10 are urged downward by the coil spring 26, and engaged by the engaging springs 253.

The dry analytical film chip conveying portion 30 is provided with a suction pad 31 which sucks to fix the dry analytical film chip 10 as the conveying means, and the suction pad 31 is connected to a suction means (not illustrated) to suck air to form reduced pressure conditions. A moving means (not illustrated) is also provided which moves the suction pad 31. By the moving means, the suction pad 31 moves horizontally between the cartridge 22 and the incubator 50, stops in the three steps of an upper part, a middle part and a lower part under the dry analytical film chip cartridge 22 and stops in the two steps of a middle part and a lower part at the incubator 50.

In the spotting portion 40, an arm 41 is provided with a pipette tip 42, and a sample liquid is spotted onto the dry analytical film chip 10 by the pipette tip 42. The arm 41 is rotatable horizontally and movable vertically, and is provided with a sample liquid container (not illustrated) wherein a sample liquid is placed.

In the incubator 50, an incubator body 51 in a disc form is rotatably supported. The incubator body 51 contains a heating means (not illustrated) which keep the inside at a constant temperature around 37° C. Many insertion holes 52 are formed on the circumferential side end of the body 51 at regular intervals for inserting the dry analytical film chip 10, and followed by placing parts 53 for placing the dry analytical film chip 10.

Figure 4:
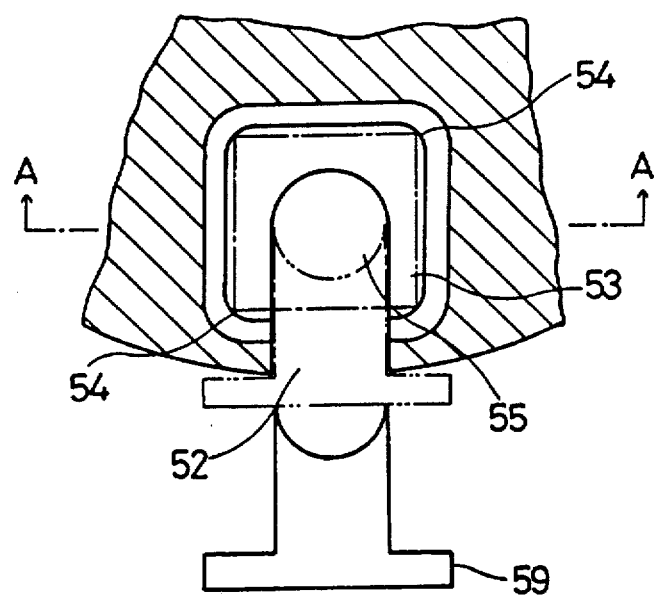
FIG. 4 is a partial transverse sectional view of the principal part of the incubator used in the above analyzer.

As shown in FIGS. 4 and 5, the placing part 53 has a rectangular planar form greater than the dry analytical film chip 10, and each corner 54 is projected toward the inside by rounding. Each corner of the dry analytical film chip 10 is caught by the rounded corner 54, and thereby the sides of the dry analytical film chip 10 do not contact the side walls of the placing part 53. A photometric window 55 is formed at the center of the placing part 53, and a ring groove 56 into which a photometric head, described later, enters is formed at the underside of the photometric window 55. A taper 57 is formed above the periphery of the placing part 53 in order to guide the dry analytical film chip 10, and a cover 58 is provided movable in the vertical direction above the placing part 55 so as to prevent the evaporation of the sample liquid. Moreover, the incubator body 51 is provided on the outside with a closing member 59 which closes the insertion hole 52 to prevent the evaporation of the sample liquid at the time of incubation.

As shown in FIG. 1, the photometric portion 60 is provided with a photometric head 61 which measures a reflection optical density of the color produced in the dry analytical film chip 10 by the coloring reaction with the sample liquid, and the top portion is close to, in contact with or fitted to the ring groove 56 of the incubator body 51. The photometric head 61 irradiates light for measurement containing a predetermined wavelength to the reagent layer 12 through the support 11, and detects the reflected light by a light detecting sensor. The photometric head 61 is connected to a light source 64 through a filter disc 65 and a lens 63. The filter disc 65 is composed of a disc plate and a plurality of filters 62 mounted onto the disc plate corresponding to the number of analytical items, and the filter 62 for each analytical item is selected by rotating the filter disc 65. The photometric head 61 is electrically connected to a operation station 67 through an amplifier 66. The operation station 67 determines the reflection optical density of the color produced in the reagent layer 12 based on the level of imputted electric signal, and the concentration or activity of a predetermined biochemical substance (analyte) in the sample liquid is calculated.

The discharging portion 70 of the dry analytical film chip 10 is provided with a discharge shoot 71 (a part is illustrated) and a suction pad 72 for conveying the dry analytical film chip 10 from the placing part 53 of the incubator body 51 to the discharge shoot 71. A slit 73 for entering the suction pad 72 is formed at the discharge shoot 71 on the side of the incubator body 51. The suction pad 72 is mounted to a traveling means (not illustrated), and travels horizontally between the placing part 53 and the discharge shoot 71 and vertically under the placing part 53 and at the discharge shoot 71.

When a sample liquid is measured by using the dry analytical film chip by operating the above analyzer, the dry analytical film chip 10 is taken out from the cartridge 22 or

80. The sample liquid is spotted onto the dry analytical film chip 10, and then the film chip 10 is conveyed to the incubator 50. That is, by reciprocating the suction pad 31 between the dry analytical film chip cartridge 22 or 80 and the incubator 50 through the spotting portion 40, a virgin dry analytical film chip 10 is taken out from the cartridge 22 or 80, and delivered to the spotting portion 40. The dry analytical film chip 10 spotted with the sample liquid is delivered to the incubator 50, and the suction pad 31 returns to the cartridge 22 or 80. Meanwhile, as shown in FIG. 1, the suction pad 31 positioned under the cartridge 22 is allowed to ascend (arrow a) to adsorb the lowermost dry analytical film chip 10 (arrow b). Subsequently, the dry analytical film chip 10 is slid in the adsorbed state toward the notch 251 to release from the holding part 252, and slightly descends to take the dry analytical film chip 10 out of the cartridge 22 or 80 (arrow c).

The sequential motion of taking out the dry analytical film chip 10 from the cartridge 22 is shown in FIG. 6. As shown in FIG. 6(*a*), the suction pad 31 is allowed to ascend from the lower part to the upper part, and as shown in FIG. 6(*b*), the lowermost dry analytical film chip 10*a* is adsorbed by the suction pad 31. Subsequently, as shown in FIG. 6(*c*), after being slid horizontally slightly, the suction pad 31 is allowed to descend. So, the dry analytical film chip 10*a* descends with widening the engaging springs 253 by the sides of the dry analytical film chip 10*a*. The widened engaging springs 253 return to the original state by its elasticity immediately after passing the dry analytical film chip 10*a* to engage the next dry analytical film chip 10*b* which was positioned at the second from the bottom. The descended suction pad 31 is, as shown the final step in FIG. 6(*d*), positioned at the middle part with adsorbing the dry analytical film chip 10*a*, and the second dry analytical film chip 10*b* is positioned at the lowermost part in the cartridge 22. Then, in FIG. 1, the suction pad 31 moves horizontally to the spotting portion 40 (arrow d), and the sample liquid is spotted by the pipette tip 42. Then, the suction pad 31 moves horizontally again to deliver the dry analytical film chip 10*a* into the incubator 50 (arrow e), and descends to lead the film chip 10*a* in the placing part 53 (arrow f).

Figure 7:
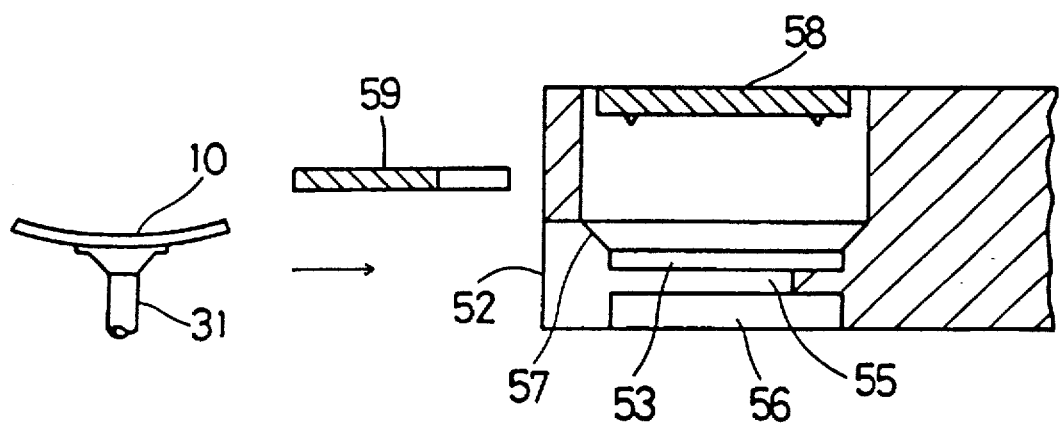
FIGS. 7 through 11 are partial sectional views of the incubator illustrating a procedure of conveying the dry analytical film chip to the incubator.
Figure 8:
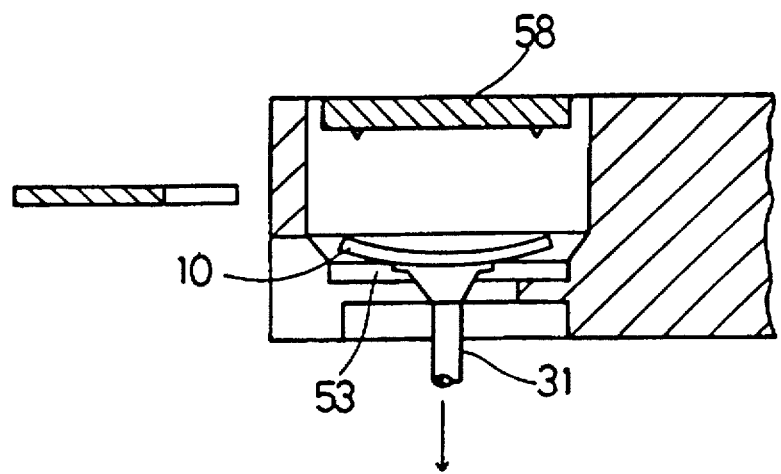
Figure 9:
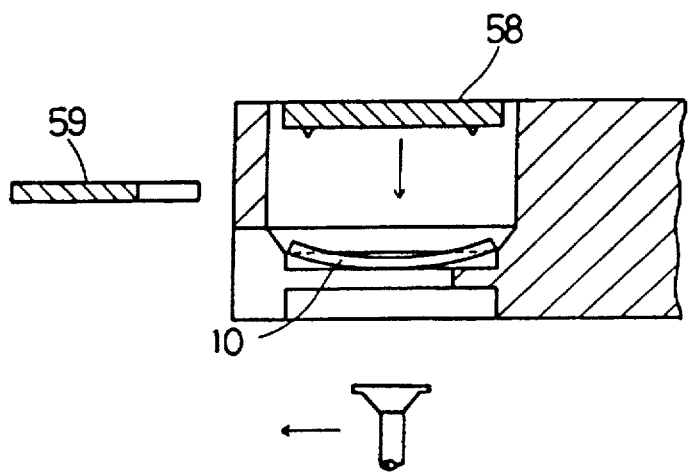
Figure 10:
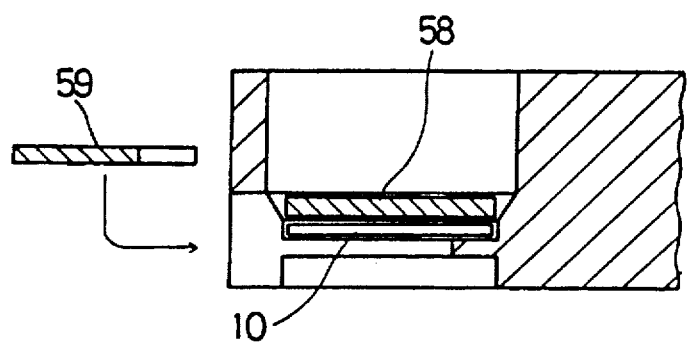
Figure 11:
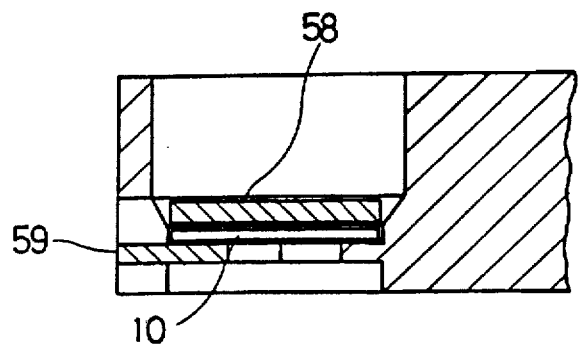

As the loading procedure of the dry analytical film chip 10 into the placing part 53 of the incubator body 51, as shown in FIG. 7, the dry analytical film chip 10 is delivered horizontally, and as shown in FIG. 8, it is passed through the insertion hole 52 to be positioned at the placing part 53. Subsequently, as shown in FIG. 9, the suction pad 31 descends to place the dry analytical film chip 10 on the placing part 53, and as shown in FIG. 10, the suction pad 31 is moved horizontally to return the lower first position, while the cover 58 descends to press the dry analytical film chip 10. Then, as shown in FIG. 11, the closing member 59 is fitted to the insertion hole 52 to render the dry analytical film chip 10 in an almost closed state.

In the above state, the dry analytical film chip 10 is incubated for a predetermined time, and the reflection optical density of the color produced in the reagent layer through the coloring reaction is measured by the photometric head 61. The light reflected from the reagent layer 12 contains light information corresponding to the amount of dye produced in the reagent layer 12 (actually light quantity), and the reflected light containing the light information enters into the light detecting sensor to convert to electricity. The electricity is delivered to the amplifier 66 and then to operation station 67. In the operation station 67, the optical density of the dye produced in the reagent layer 12 is calculated based on the level of the inputted electric signal, and the concentration or activity of the predetermined biochemical substance in the sample solution is calculated.

The dry analytical film chip 10 after the photometry has been finished is delivered to the discharging portion, and adsorbed by the suction pad 72. Then, it is taken out of the incubator body 51, and conveyed to the slit 73 of the discharge shoot 71. The suction pad 72 descends to release the dry analytical film chip 10 on the discharge shoot 71, and the released dry analytical film chip 10 is put in a recovering container through the discharge shoot 71.

Figure 12:
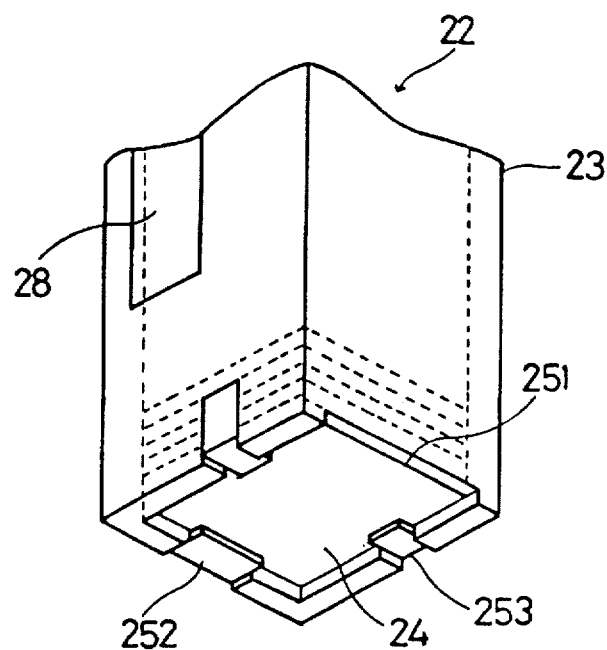
FIGS. 12 through 14 are partial perspective views of the lower part of respective cartridges for storing dry analytical film chips separately embodying the invention viewed from the underside.
Figure 13:
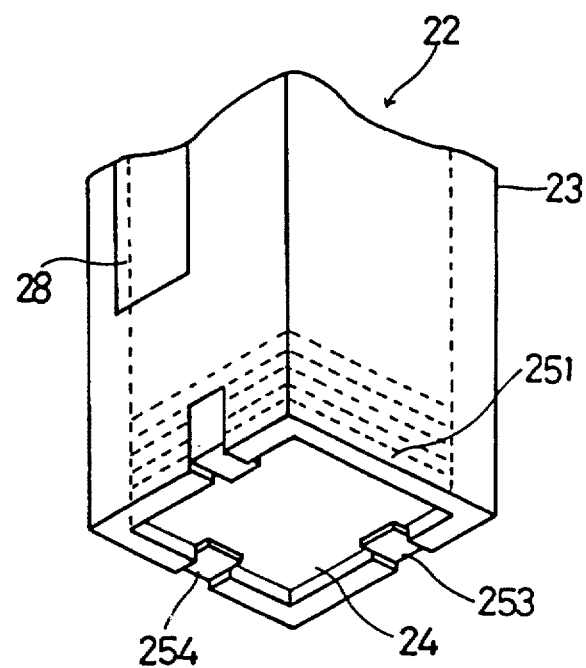
Figure 14:
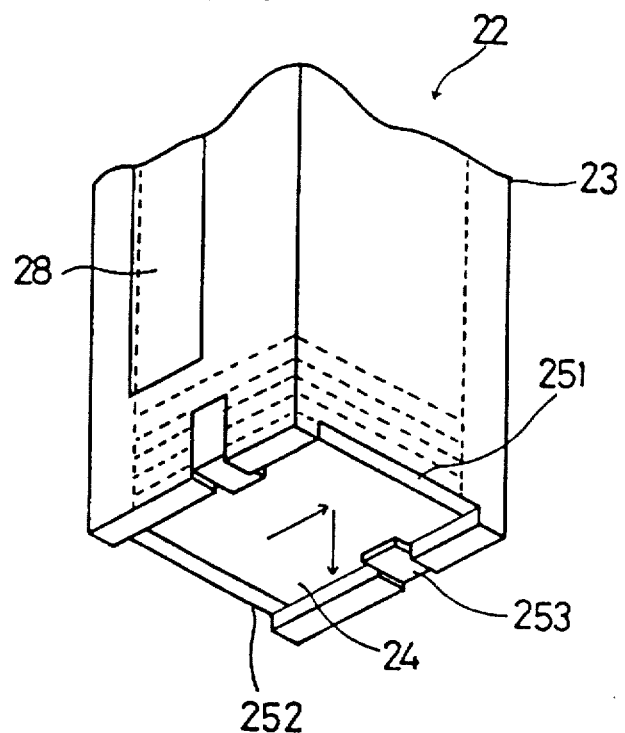

Some modifications of the cartridge are shown in FIGS. 12 through 14.

In the cartridge of FIG. 12, the holding part 252 is made of a slender metal plate having substantially no elasticity, and is fixed by embedding. The motion for taking out the dry analytical film chip from the cartridge 22 is similar to the aforementioned one.

In the cartridge of FIG. 13, the notch 251 is not formed, and the opposite side is provided with an engaging spring 254 having elasticity made of the same material as the engaging spring 253. The dry analytical film chip 10 is taken out from the cartridge by adsorbing the lowermost dry analytical film chip 10 by the suction pad 31 followed by moving the suction pad 31 downward as it is.

In the cartridge of FIG. 14, two notches 251 are formed at a pair of facing ends. The dry analytical film chip 10 is taken out from the cartridge by sliding horizontally followed by descending as the cartridge shown in FIG. 3, or by directly moving downward as the cartridge shown in FIG. 14.

Example 2

Figure 16:
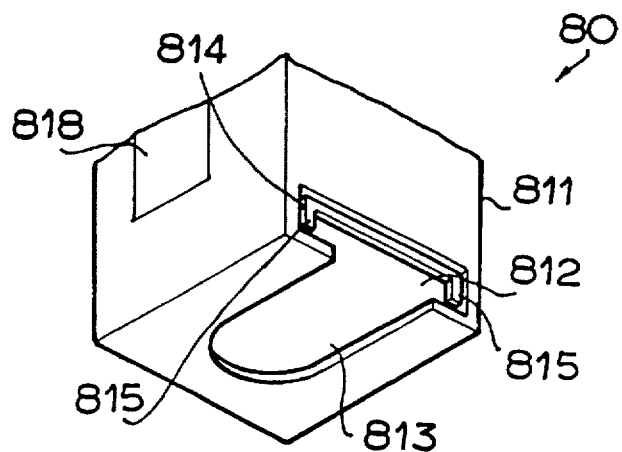
FIG. 16 is a partial perspective view of the lower part of another cartridge for storing dry analytical film chips embodying the invention looked at from the underside.
Figure 17:
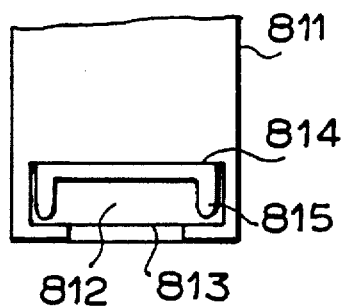
FIG. 17 is a partial front view thereof and FIG. 18 is a partial sectional view thereof, respectively.
Figure 18:
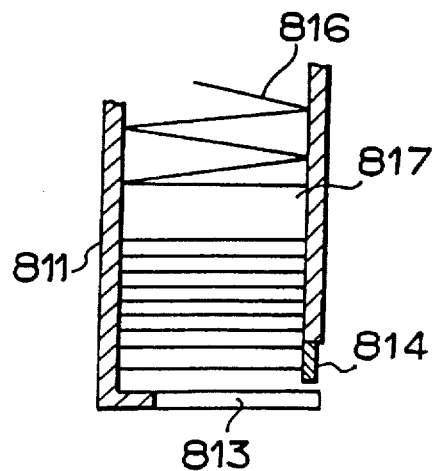

An example of the cartridge is shown in FIGS. 16 through 18.

The cartridge 80 of this example is composed of a casing 811 in a form of hollow rectangular parallelepiped having an outer size of about 18 mm×18 mm×100 mm and a thickness of about 1 to 2 mm, and formed of an organic polymer colored black so as to have light-shielding ability. An exit 812 for taking out the dry analytical film chip 10 is formed at the lower end of a side wall of the casing 811. A U-shaped notch 813 is formed at the bottom of the casing 811 so as to connect the exit 812 for adsorbing the lowermost dry analytical film chip 10 by the conveying means and moving horizontally in the direction to the exit 812.

A flexible engaging means 814 made of PET or polypropylene sheet 100 µm in thickness having elasticity is fixed to the wall having the exit 812 in the direction parallel to the wall, i.e. the direction of the extension of the wall, so that the inner surface almost conforms to the extension of the inner surface of the wall of the casing 811. In the flexible engaging means 814, two engaging tongue portions 815 having a length of about 500 µm are projected downward from both ends. The distance between both tongue portions 815 is made so that the central portion of the top of each tongue portion is positioned about 1 mm apart from the side edge of the dry analytical film 10. Both corners of side edge of the each tongue portion are rounded so as to has a U form section. Similar to Example 1, a coil spring 816 for pushing the dry analytical film chips 10 downward is fixed to the reverse side of the top of the casing 811, and a push plate 817 having a similar size to the dry analytical film chip 10 is fixed to the lower end of the coil spring 816.

A magnetic code 818 is provided on the outer surface of the casing 811 as shown in FIG. 16. The magnetic code 818 has been recorded with various information, such as the kind of the stored dry analytical film chips 10, lot number, lot-specific information data for correction, analyte (analytical item), shelf life, and the like. This information is read by a magnetic head (not illustrated) and utilized for the biochemical analysis at a control station (not illustrated).

The dry analytical film chip cartridge 80 has the structure as above, and many dry analytical film chips 10 are loaded therein in a state that the support 11 is positioned on the underside, i.e. the spreading layer 13 (or the reagent layer 12) is positioned on the upper side. The stack of the dry analytical film chips 10 are urged downward by the coil spring 816.

Figure 19A:
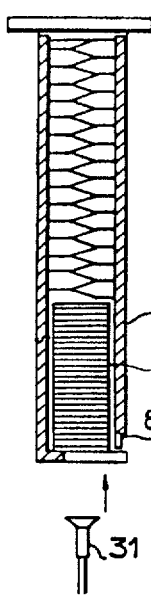
FIGS. 19(a), 19(b), 19(c) and 19(d) illustrate a procedure of taking out one dry analytical film chip from the cartridge shown in FIG. 16 through 18.
Figure 19B:
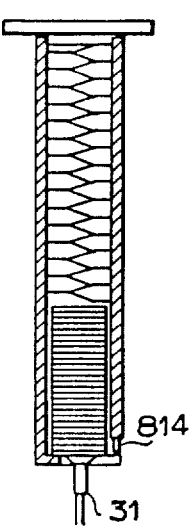
Figure 19C:
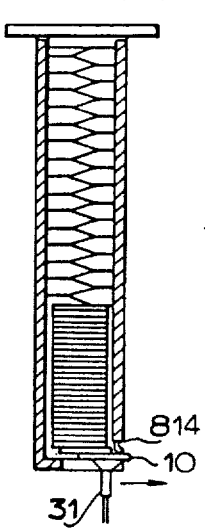
Figure 19D:
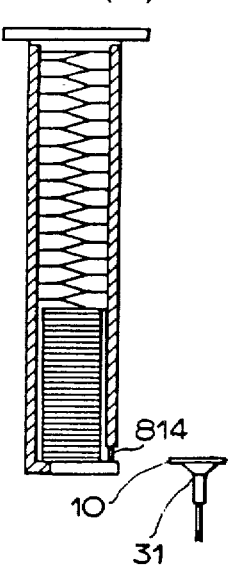

When the dry analytical film chip 10 is taken out from the above cartridge, as shown in FIG. 19, the procedure commences as shown in FIG. 19(A) and the underside of the support of the lowermost analytical film chip as seen in FIG. 19(B) 10 is sucked by the suction pad 31 as the conveying means to fix it through the U-shaped notch 813 of the cartridge bottom. Then, the suction pad 31 is moved horizontally toward the exit 812 along the U-shaped notch 813, and while, the dry analytical film chip 10 adsorbed by the suction pad 31 moves with widening the flexible engaging means 814 as seen in FIG. 19(C). The suction pad 31 continues to move horizontally as it is until the dry analytical film chip 10 reaches the outside of the cartridge 80 as seen in FIG. 19(D). At that time, the second dry analytical film chip 10 positioned on the lowermost one is trailed by the friction. However, the flexible engaging means 814 inhibits the second dry analytical film chip 10 to leave in the casing 811.

Figure 20A:
FIG. 20(A) illustrates two separate squamaform pieces.
Figure 20B:
FIG. 20(B) illustrates two separate tongue pieces.
Figure 20C:
FIG. 20(C) illustrates two separate long tongue pieces.
Figure 20D:
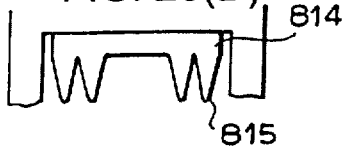
FIG. 20(D) illustrates two acute angular tongue portions.
Figure 21:
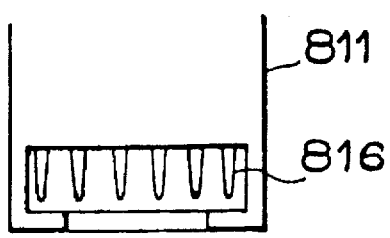
Figure 22:
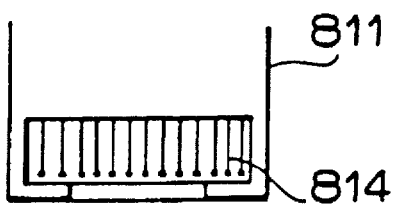

Some modifications of the cartridge 80 are illustrated in FIGS. 20 through 22.

In the cartridge of FIG. 20(A), the flexible engaging means 814 is composed of two separate squamaform pieces.

In the cartridge of FIG. 20(B), the flexible engaging means 814 is composed of two separate tongue pieces.

In the cartridge of FIG. 20(C), the flexible engaging means 814 is composed of two separate long tongue pieces.

In the cartridge of FIG. 20(D), the flexible engaging means 814 is formed integrally, and two acute angular tongue portions for engaging 815 are formed on both sides.

In the cartridge of FIG. 21, several rows of elastic single fiber loops of a hook-and-loop fastener are provided as the flexible engaging means 816.

In the cartridge of FIG. 22, several rows of elastic single fiber are provided as the flexible engaging means 814.

Example 3

Another example of the cartridge is shown in FIGS. 23 through 29.

The cartridge 80 of this example is also provided with an exit 822 formed on the lower part of the casing 821 and a hole 824 for the suction pad 31 formed on the bottom end panel 823. Two flexible engaging means 825 for the lowermost film chip are formed at the lower part of the front of the casing 821, and an engaging means 826 for the second film chip is formed between the flexible engaging means 825, 825. The flexible engaging means 825 for the lowermost film chip are formed integrally with the casing 821 so that the width and the thickness are gradually smaller from the base end to the top, and thereby, it is made deformable. The top of the flexible engaging means 825 for engaging the lowermost film chip is lengthened to the position to engage the lowermost film chip, and in the usual conditions, it prevents the lowermost dry analytical film chip 10 so as not to go out.

The engaging means 826 for the second film chip is also integrally formed with the casing 821, and it is not easily bent. The top is lengthened to the position to engage the second dry analytical film chip 10 positioned on the lowermost dry analytical film chip 10, and prevents the second film chip 10 form going out trailed by the lowermost film chip 10.

A push plate 827 and a coil spring 828 which contacts the push plate 827 as the urging means are provided in the casing 821, and the dry analytical film chips 10 loaded therein are always pushed toward the end panel 823 by the coil spring 828 through the push plate 827. A bar 829 is provided in the coil spring 828 so that the dry analytical film chips 10 do not stand. That is, when the cartridge 80 is erroneously dropped, some dry analytical film chips become occasionally vertically (parallel to the wall of the casing) during contracting the coil spring 827 by the drop shock. However, the above bar 829 holds the push plate 827 while the coil spring 827 is contacted, and accordingly, the dry analytical film chips do not stand by the drop shock.

Each two vertical ribs 830 are formed on 4 inner wall surfaces of the casing 821 so that the movement of the dry analytical film chips 10 in the casing 821 is rendered smooth.

Figure 29:
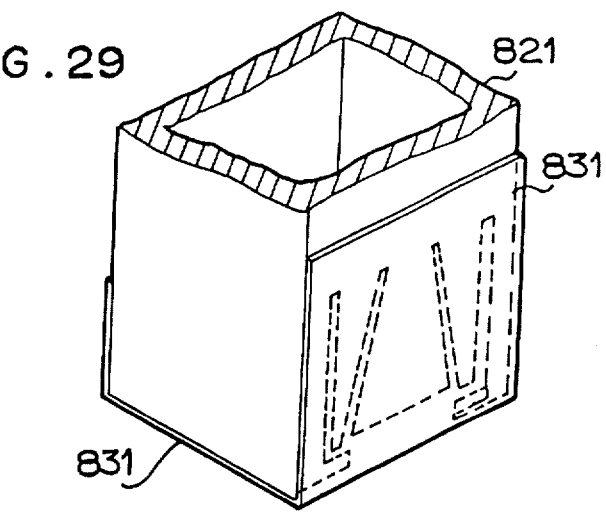
FIG. 29 is a partial perspective view of the lower part of the cartridge of FIG. 23 in the state of not use.
Figure 30:
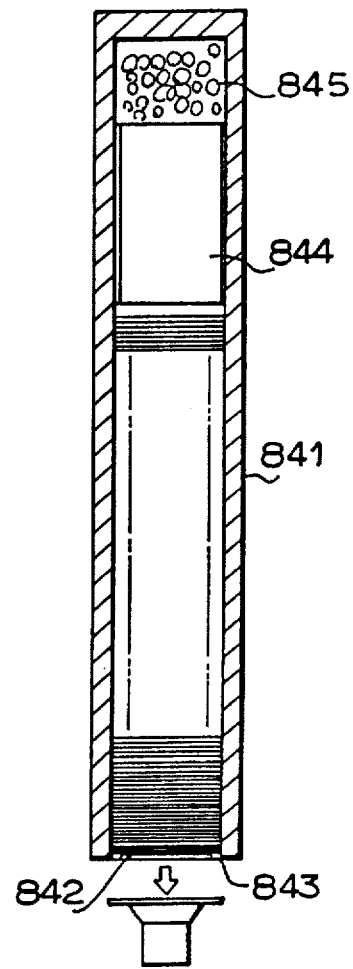
FIG. 30 is a sectional view of another cartridge for storing dry analytical film chips embodying the invention.
Figure 31:
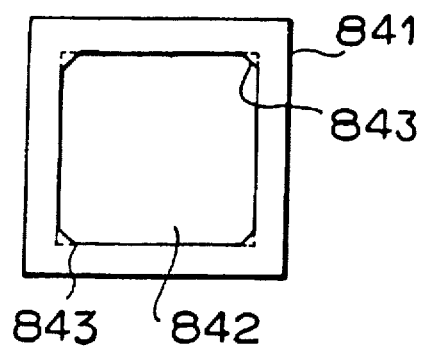
FIG. 31 is a bottom view thereof.
Figure 32:
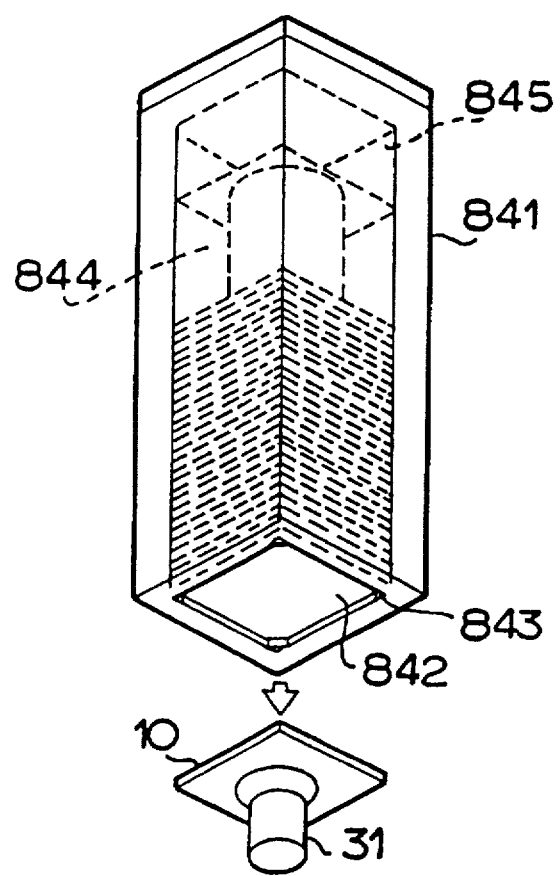
FIG. 32 is a perspective view thereof viewed from the underside.

The cartridge 80 is, as shown in FIG. 29, sealed by closing the exit 822, the hole 824, etc. by adhering an adhesive tape 831 prior to use.

Figure 23:
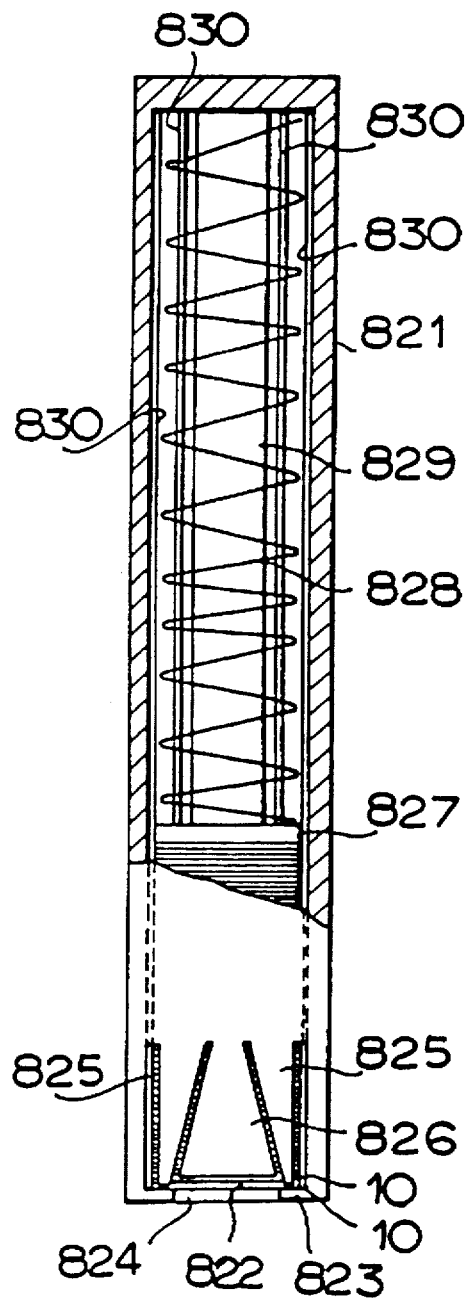
FIG. 23 is a front view of another cartridge for storing dry analytical film chips embodying the invention of which the upper part is a section.
Figure 24:
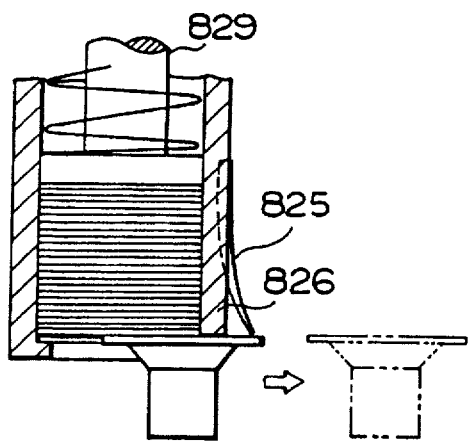
FIG. 24 is a partial side section of the lower part thereof.
Figure 25:
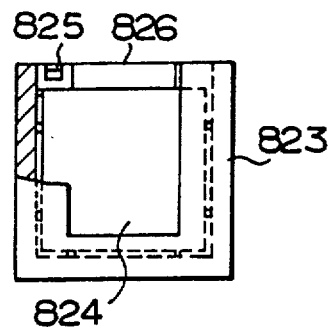
FIG. 25 is a bottom view thereof.
Figure 26:
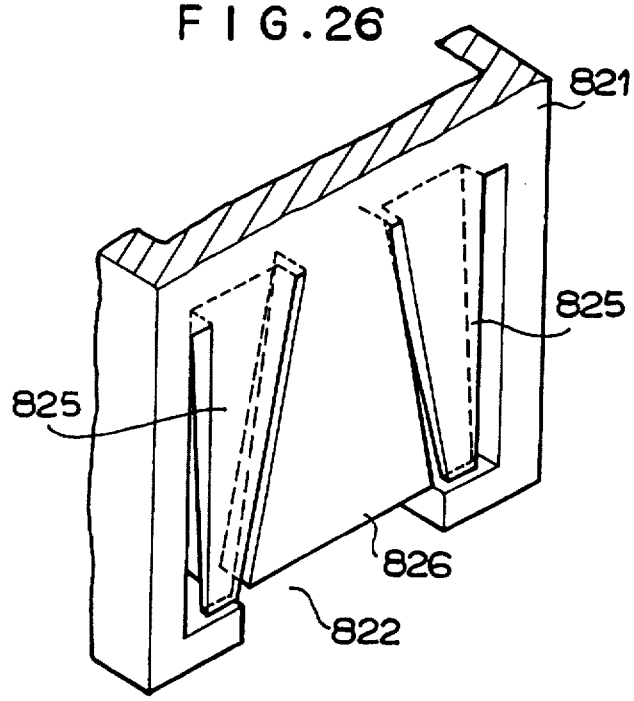
FIG. 26 is an enlarged perspective view of the flexible engaging means portion of the cartridge of FIG. 23.

When the dry analytical film chip 10 is taken out from the above cartridge, as shown in FIG. 28, the underside of the support of the lowermost analytical film chip 10 is sucked by the suction pad 31 to fix it through the hole 824 of the cartridge bottom, see FIG. 23. The individual steps are shown in FIG. 28(A), FIG. 28(B), FIG. 28(C) and FIG. 28(D) and follow the procedure described in connection with FIGS. 19(A), 19(B), 19(C) and 19(D), respectively. Then, the suction pad 31 is moved horizontally toward the exit 822 along the hole 824, the FIG. 28(B) position, until the dry analytical film chip 10 reaches the outside of the cartridge 80, the FIG. 28(C) position. At that time, the second dry analytical film chip 10 positioned on the lowermost one is trailed by the friction. However, the engaging means 826 for the second film chip inhibits the second dry analytical film chip 10 from leaving in the casing 811.

Example 4

Another example of the cartridge is shown in FIGS. 30 through 34.

The cartridge 80 of this example is composed of a casing 841 in a form of hollow rectangular parallelepiped having an outer size of about 18 mm×18 mm×100 mm and a thickness of about 1 mm, and formed of an organic polymer colored black so as to have light-shielding ability. An exit 842 for taking out of the dry analytical film chip 10 is formed at the bottom of the casing 841. Non-flexible engaging means 843 having a right-angled equilateral triangle form having a side of about 1000 μm and a thickness of about 1000 μm are mounted at 4 corners of the exit 842.

A weight 844 is put on the push plate 843 in the casing 841 as the urging means for pushing the dry analytical film chips 10, and cushioning materials 845 are filled in the space above the weight 844. The cushioning materials 845 prevent the dry analytical film chips from standing by dropping the cartridge before use.

As shown in FIG. 33, a cap 845 is fitted to seal the lower end before use.

When the dry analytical film chip 10 is taken out from the above cartridge, as shown in FIG. 34, the suction pad 31 is allowed to ascend, and sucks the underside of the support of the lowermost analytical film chip 10 to fix it through the exit 842. FIGS. 34(A), 34(B), 34(C) and 34(D) also illustrate the sequential steps in the procedure. Subsequently, the suction pad 31 is moved vertically downward. Then, the movement of the lowermost dry analytical film chip 10 is inhibited at four corners by the non-flexible engaging means 843 to deform. The lowermost dry analytical film chip 10 passes the non-flexible engaging means 843 in the deformed state, and is conveyed downward. The second dry analytical film chip 10 is placed on the non-flexible engaging means 843 immediately after the lowermost dry analytical film chip 10 passes the exit 842.

Example 5

Another example of the cartridge is shown in FIGS. 35 and 36. In this example, FIGS. 36(A), 36(B), 36(C) and 36(D), respectively follow the same sequential steps as in FIGS. 34(A), 34(B), 34(C) and 34(D).

The cartridge 80 of this example is provided with a casing 851, an exit 852 and a push plate 853 similar to Example 4, and instead of the weight 844, a coil spring 854 is provided as the urging means. A flexible engaging means 855 formed by bending a metal wire at almost a right angle is provided at four corners of the exit 852 formed by opening the bottom of the casing 851. The flexible engaging means 855 has a strength capable of holding the stack of the dry analytical film chips 10 even at the maximum loading, and is bent downward to widen the exit 852 when the lowermost dry analytical film chip 10 is drawn downward by the suction pad 31.

When the dry analytical film chip 10 is taken out from the above cartridge, as shown in FIG. 36, the suction pad 31 is allowed to ascend, and sucks the underside of the support of the lowermost analytical film chip 10 to fix it through the exit 852. Subsequently, the suction pad 31 is moved vertically downward. Then, the dry analytical film chip 10 is bowed downward, and the flexible engaging means 855 is bent downward to discharge the dry analytical film chip 10 passing through the exit 852. The second dry analytical film chip 10 is placed on the flexible engaging means 855 immediately after the lowermost dry analytical film chip 10 passes the exit 852.

Figure 37:
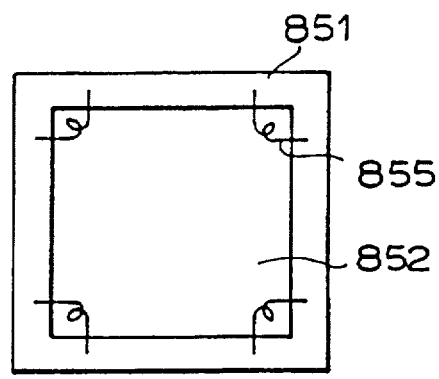
FIG. 37 is a bottom view of a modification of the cartridge of FIG. 35 wherein the flexible engaging means is modified.
Figure 38:
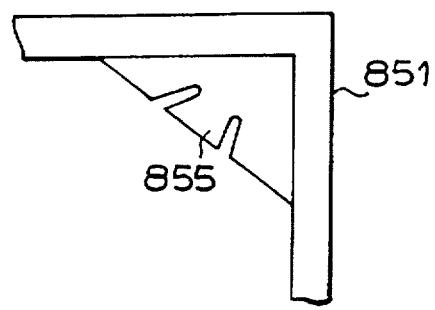
FIG. 38 is a partial enlarged bottom view of another modification of the cartridge of FIG. 35 wherein the flexible engaging means is modified.
Figure 39:
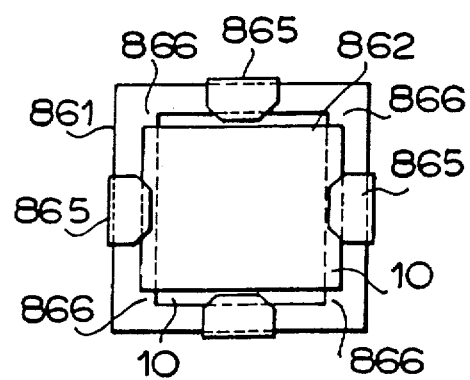
FIG. 39 is a bottom view of another cartridge for storing dry analytical film chips embodying the invention.
Figure 40:
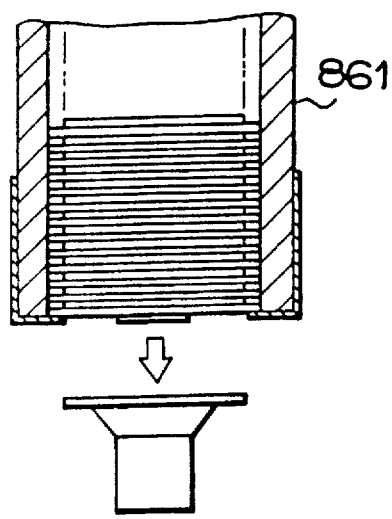
FIG. 40 is a sectional view of the lower part thereof.
Figure 41:
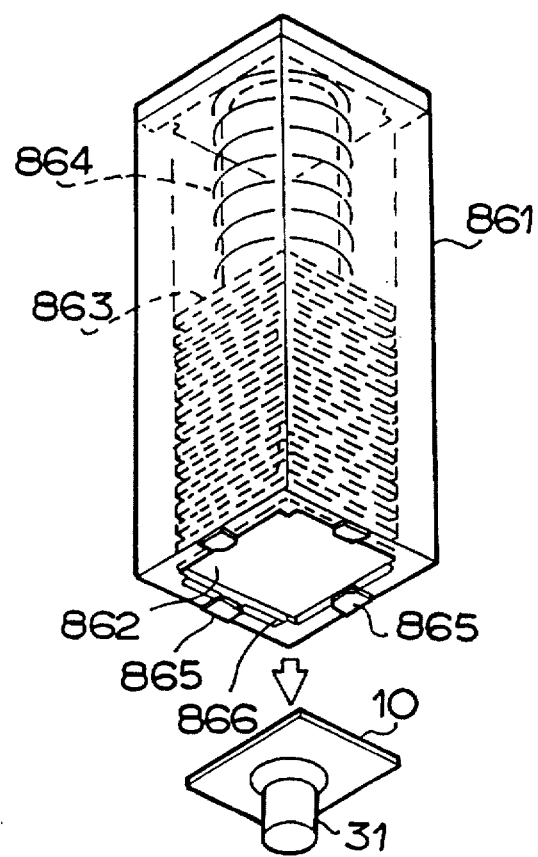
FIG. 41 is a perspective view thereof viewed from the underside.
Figure 42A:
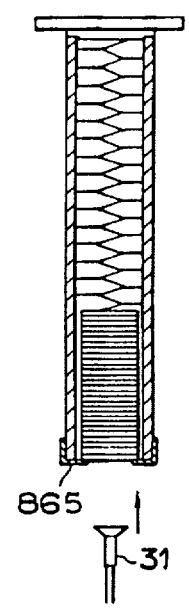
FIGS. 42(A), 42(B), 42(C) and 42(D) illustrate a procedural sequence of taking out one dry analytical film chip from the cartridge of FIG. 39.
Figure 42B:
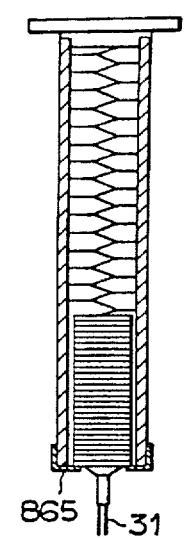
Figure 42C:
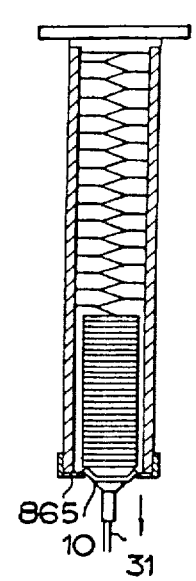
Figure 42D:
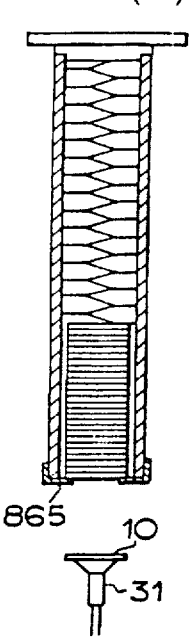

Some modifications of the cartridge 80 are illustrated in FIGS. 37 and 38.

In the cartridge of FIG. 37, the flexible engaging means 855 is the same as shown in FIG. 35, except that the metal wire is once coiled to form a loop at the corner.

In the cartridge of FIG. 38, the flexible engaging means 855 is composed of a triangular metal plate, and two notches are formed at the oblique line part in order to impart flexibility.

Example 6

Another example of the cartridge is shown in FIGS. 39 through 42. FIGS. 42(A), 42(B), 42(C) and 42(D) respectively follow the same sequential steps as FIGS. 36(A), 36(B), 36(C) and 36(D), while using different specific features.

The cartridge 80 of this example is provided with a casing 861, an exit 862 and a push plate 863 similar to Example 4, and instead of the weight 844, a coil spring 864 is provided as the urging means. Non-flexible engaging means 865 made of a metal plate are mounted at four sides of the exit 862 in a state projected into the exit 862. Square guides 866 are formed at four corners of the exit 862. Rectangular dry analytical film chips are stacked by turns, and the lowermost dry analytical film chip 10 is held by the non-flexible engaging means 865 located corresponding to the shorter sides of the chip 10.

When the dry analytical film chip 10 is taken out from the above cartridge, as shown in FIG. 42, the suction pad 31 is allowed to ascend, and sucks the underside of the support of the lowermost analytical film chip 10 to fix it through the exit 862. Subsequently, the suction pad 31 is moved vertically downward. Then, the movement of the film chip 10 is inhibited by the non-flexible engaging means 865 opposite to each other, and is curved. The dry analytical film chip 10 passes the non-flexible engaging means 865 in the curved state, and is conveyed downward. The second dry analytical film chip 10 is placed on the non-flexible engaging means 865 immediately after the lowermost dry analytical film chip 10 passes the exit 862.

Figure 43:
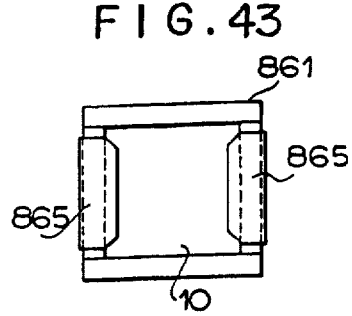
FIG. 43 is a bottom view of a modification of the cartridge of FIG. 39 wherein the non-flexible engaging means is modified.
Figure 44:
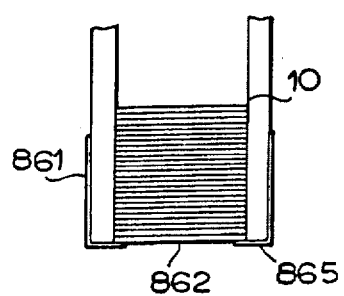
FIG. 44 is a sectional view of the lower part thereof.

A modification of the cartridge is illustrated in FIGS. 43 and 44. In this cartridge, the non-flexible engaging means 865 are provided only on two sides opposite to each other of the exit 862 provided by opening the bottom of the casing 861. All dry analytical film chips 10 are held by the two non-flexible engaging means 865.

Example 7

Another example of the cartridge is shown in FIGS. 45 and 46.

The cartridge 80 of this example is provided with a casing 871, an exit 872 and the like similar to Example 4, and a row of elastic single fiber loops 873 of hook-and-loop fastener is provided on the sides opposite to each other of the exit 872 formed at the lower end of the casing 871. In the cartridge, the loops 873 hold the lowermost dry analytical film chip 10, deform to discharge the dry analytical film chip 10 through the exit 872 at the time of taking out.

A modification of the cartridge is illustrated in FIGS. 47 and 48. In this cartridge, 4 rows of elastic single fiber loops 873 are provided.

We claim:

1. A cartridge for storing dry analytical film chips which comprises:

a casing wherein a plurality of the dry analytical film chips without a slide frame having at least one reagent layer provided on a support are stacked;

an exit for taking out the lowermost dry analytical film chip of the stack one by one;

urging means for pushing the dry analytical film chip stack without the slide frame toward the exit;

engaging means for inhibiting the discharge in a lateral direction of the lowermost dry analytical film chip of the stack from the casing; and conveying means for the dry analytical film chip, and an opening for passing the conveying means of the dry analytical film chip to be taken out through said opening;

wherein:
the exit and the engaging means for inhibiting the discharge of the lowermost dry analytical film chip are provided at the lower end portion of one side wall of the casing, and said casing including a second closed side wall opposite to said one side wall provided with said exit;

the opening being provided at the bottom of the casing; and the engaging means for inhibiting the discharge of the lowermost dry analytical film chip is a flexible engaging means comprising tongue portions for releasing the lowermost dry analytical film chip when it is discharged by the conveying means and holding the second lowermost dry analytical film chip whereby the dry analytical film chip is taken out of the cartridge from the underside thereof.

2. The cartridge of claim 1, wherein the tongue portions have a form selected from the group consisting of a tongue, a squamation, an inverted triangle and a wedge.

3. The cartridge of claim 1, wherein the flexible engaging means is composed of loops or straight lines of an elastic single fiber.

4. The cartridge of claim 1, wherein the casing has an inside diameter slightly greater than the dry analytical film chips stacked having a side or diameter of 8 to 20 mm.

5. The cartridge of claim 1, wherein the tongue portions have an inverted U form or II form.

6. The cartridge of claim 5, wherein the tongue portions are positioned about 0.5 mm to 1 mm apart from the side edge of the dry analytical film chip toward the inside of the dry analytical film chip.

7. The cartridge of claim 1, wherein the tongue portions have a thickness smaller than the wall thickness, a maximum width of 1 to 3 mm and a length of 250 μm to 3 mm.

8. The cartridge of claim 1, wherein the conveying means is a suction pad.

9. A cartridge for storing dry analytical film chips which comprises:

a casing wherein a plurality of the dry analytical film chips having at least one reagent layer provided on a support are stacked;

an exit for taking out the lowermost dry analytical film chip of the stack one by one;

urging means for pushing the dry analytical film chip stack toward said exit;

engaging means for inhibiting the discharge of the lowermost dry analytical film chip of the stack from said casing; and an opening for passing the conveying means of the dry analytical film chip to be taken out;

wherein:
the exit and the engaging means for inhibiting the discharge of the lowermost dry analytical film chip are provided at an end portion of a first side wall of said casing and said casing having a second side wall opposite to said first side wall, said second side wall being closed;

said opening being provided at the bottom of the casing;

the engaging means for inhibiting the discharge of the lowermost dry analytical film chip is composed of tongue portions defining flexible engaging means for the lowermost film chip for releasing the lowermost dry analytical film chip by the conveying means so that the dry analytical film chip is taken out from the underside of said cartridge; and additional flexible engaging means for holding the second lowermost dry analytical film chip.

10. The cartridge of claim 9, wherein said additional flexible engaging means holds the second end dry analytical film chip when the end dry analytical film chip is discharged.

11. The cartridge of claim 9, wherein the lower end of the engaging means holding the second end dry analytical film chip is positioned between the upper side and the underside of the second lowermost dry analytical film chip and has a rigidity for keeping it.

12. The cartridge of claim 9, wherein the casing has an inside diameter slightly greater than the dry analytical film chips stacked having a side or diameter of 8 to 20 mm.

13. The cartridge of claim 9, wherein the tongue portions have an inverted U form or II form and the engaging means capable of holding the second end dry analytical film chip is positioned between the tongue portions.

14. The cartridge of claim 13, wherein the tongue portions are positioned about 0.5 mm to 1 mm apart from the side edge of the dry analytical film chip toward the inside of the dry analytical film chip.

15. The cartridge of claim 9, wherein the tongue portions have a thickness smaller than the wall thickness, a maximum width of 1 to 3 mm and a length of 250 μm to 3 mm.

16. The cartridge of claim 9, wherein the conveying means is a suction pad.

17. A cartridge for storing dry analytical film chips free of any slide frame which comprises:

a casing wherein a plurality of the frameless dry analytical film chips having at least one reagent layer provided on a support are stacked;

an exit for taking out the lowermost dry analytical film chip of the stack one by one;

urging means for pushing the dry analytical film chip stack toward said exit;

engaging means for inhibiting the discharge of the lowermost dry analytical film chip of the stack from said casing in a horizontal direction;

suction conveying means for the frameless dry analytical film chips; and an opening for passing the suction conveying means of the dry analytical film chip to be taken out;

wherein:
the exit and the engaging means for inhibiting the discharge of the lowermost dry analytical film chip are provided at an end portion of a first side wall of said casing and said casing having a second side wall opposite to said first side wall, said second side wall being closed;

said opening being provided at the bottom of the casing;

the engaging means for inhibiting the discharge of the lowermost dry analytical film chip is composed of tongue portions defining flexible engaging means for the lowermost film chip for releasing the lowermost dry analytical film chip by the suction conveying means so that the frameless dry analytical film chip is taken out from the underside of said cartridge; and additional flexible engaging means for holding the second lowermost frameless dry analytical film chip.

18. The cartridge of claim 17, wherein the tongue portions are positioned about 0.5 mm to 1 mm apart from a side edge of the frameless dry analytical film chip toward the inside of the dry analytical film chip.

19. The cartridge of claim 17, wherein the tongue portions have a thickness smaller than the wall thickness, a maximum width of 1 to 3 mm and a length of 250 μm to 3 mm.

20. The cartridge of claim 17, wherein the suction conveying means is a suction pad.

21. The cartridge of claim 17, wherein the casing has an inside diameter slightly greater than the dry analytical film chips stacked having a side or diameter of 8 to 20 mm.

22. The cartridge of claim 17, wherein the tongue portions have an inverted U form or Π form and the engaging means capable of holding the second end dry analytical film chip is positioned between the tongue portions.

23. The cartridge of claim 17, wherein the lower end of the engaging means holding the second end dry analytical film chip is positioned between the upper side and the underside of the second lowermost dry analytical film chip and has a rigidity for keeping it.

* * * * *